(12) United States Patent
Fujita et al.

(10) Patent No.: US 10,729,800 B2
(45) Date of Patent: Aug. 4, 2020

(54) CARTRIDGE FOR PERFUMING DEVICE AND PERFUMING DEVICE

(71) Applicant: Sony Corporation, Tokyo (JP)

(72) Inventors: Shuji Fujita, Tokyo (JP); Yukari Tsunoda, Tokyo (JP); Tsunetoshi Samukawa, Kanagawa (JP); Jusuke Shimura, Kanagawa (JP)

(73) Assignee: Sony Corporation, Tokyo (JP)

( * ) Notice: Subject to any disclaimer, the term of this patent is extended or adjusted under 35 U.S.C. 154(b) by 308 days.

(21) Appl. No.: 15/548,690

(22) PCT Filed: Oct. 23, 2015

(86) PCT No.: PCT/JP2015/079942
§ 371 (c)(1),
(2) Date: Aug. 3, 2017

(87) PCT Pub. No.: WO2016/143188
PCT Pub. Date: Sep. 15, 2016

(65) Prior Publication Data
US 2018/0028709 A1    Feb. 1, 2018

Related U.S. Application Data

(60) Provisional application No. 62/130,217, filed on Mar. 9, 2015.

(51) Int. Cl.
*A61L 9/12*     (2006.01)
*A45D 34/02*    (2006.01)
*A45D 34/00*    (2006.01)

(52) U.S. Cl.
CPC ............... *A61L 9/12* (2013.01); *A45D 34/02* (2013.01); *A61L 9/122* (2013.01);
(Continued)

(58) Field of Classification Search
CPC .................................. A61L 9/12; A61L 9/122
See application file for complete search history.

(56) References Cited

U.S. PATENT DOCUMENTS 5,023,020 A * 6/1991 Machida ................. A61L 9/122
                                                    239/305
5,565,148 A * 10/1996 Pendergrass, Jr. ...... A61L 9/122
                                                    261/30
(Continued)

FOREIGN PATENT DOCUMENTS

CN    101098716    1/2008
CN    201451681    5/2010
(Continued)

OTHER PUBLICATIONS

Japan Patent Office, Written Opinion for PCT Application No. PCT/JP2015/079942, dated Jan. 19, 2016.
(Continued)

*Primary Examiner* — Donald R Spamer
(74) *Attorney, Agent, or Firm* — K&L Gates LLP

(57) ABSTRACT

[Object] It is possible to efficiently perfume using a relatively small amount of fragrance material while an increase in size of a perfuming device is minimized.

[Solution] Provided is a cartridge for a perfuming device, including: a main body part; an air flow channel that is provided in the main body part and has both ends that are open; and a fragrance material held in at least a part of an inner surface of the air flow channel.

9 Claims, 31 Drawing Sheets

(52) U.S. Cl.
CPC ..... *A45D 2034/005* (2013.01); *A61L 2209/12* (2013.01); *A61L 2209/132* (2013.01); *A61L 2209/133* (2013.01)

(56) References Cited

U.S. PATENT DOCUMENTS

| | | | |
|---|---|---|---|
| 5,572,800 A | 11/1996 | West | |
| 6,399,027 B1* | 6/2002 | Shah | ............ A61L 9/042 422/1 |
| 2011/0226866 A1 | 9/2011 | Kim et al. | |
| 2014/0331622 A1* | 11/2014 | Gruenbacher | ......... B01D 46/42 55/361 |

FOREIGN PATENT DOCUMENTS

| | | |
|---|---|---|
| EP | 1 561 477 | 10/2005 |
| EP | 1451477 A1 | 10/2005 |
| JP | 1-123932 | 5/1989 |
| JP | 05-082442 | 11/1993 |
| JP | 08-504606 | 5/1996 |
| JP | 11-501834 | 2/1999 |
| JP | 2003-061545 | 4/2003 |
| JP | 2008-278770 | 11/2008 |
| JP | 5288573 | 9/2013 |
| JP | 2014-067293 | 4/2014 |
| WO | 93/08676 | 5/1993 |
| WO | 2008/072744 | 6/2008 |
| WO | 2014/182987 | 11/2014 |

OTHER PUBLICATIONS

Japan Patent Office, International Search Report for PCT Application No. PCT/JP2015/079942, dated Jan. 19, 2016.
European Search Report dated Oct. 16, 2018 in corresponding European Application No. 15884672.5.
Extended European Search Report dated Feb. 6, 2019 in corresponding European Application No. 15884672.5.
Japanese Office Action dated Aug. 27, 2019 in corresponding Japanese Application No. 2017-504561.
Chinese Office Action dated Sep. 12, 2019 in corresponding Chinese Application No. 201580077297.4.
Japanese Office Action dated Apr. 7, 2020 in corresponding Japanese Application No. 2017-504561.

* cited by examiner

FIG. 31

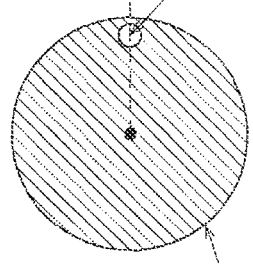
FIRST MASK: ROTATION=0°
SECOND MASK: ROTATION=0°
OVERLAPPING OF AIR FLOW CHANNEL AND OPENING

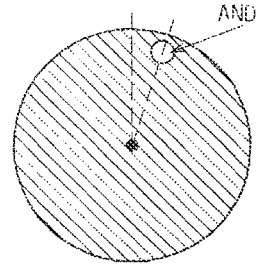
FIRST MASK: ROTATION=18°
SECOND MASK: ROTATION=18°
OVERLAPPING OF AIR FLOW CHANNEL AND OPENING

CARTRIDGE/ FIRST AND SECOND MASKS

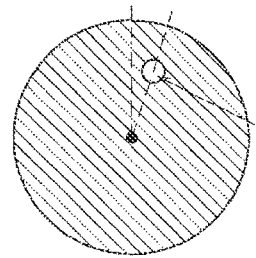
FIRST MASK: ROTATION=18°
SECOND MASK: ROTATION=0°
OVERLAPPING OF AIR FLOW CHANNEL AND OPENING

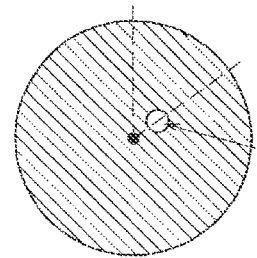
FIRST MASK: ROTATION=54°
SECOND MASK: ROTATION=0°
OVERLAPPING OF AIR FLOW CHANNEL AND OPENING

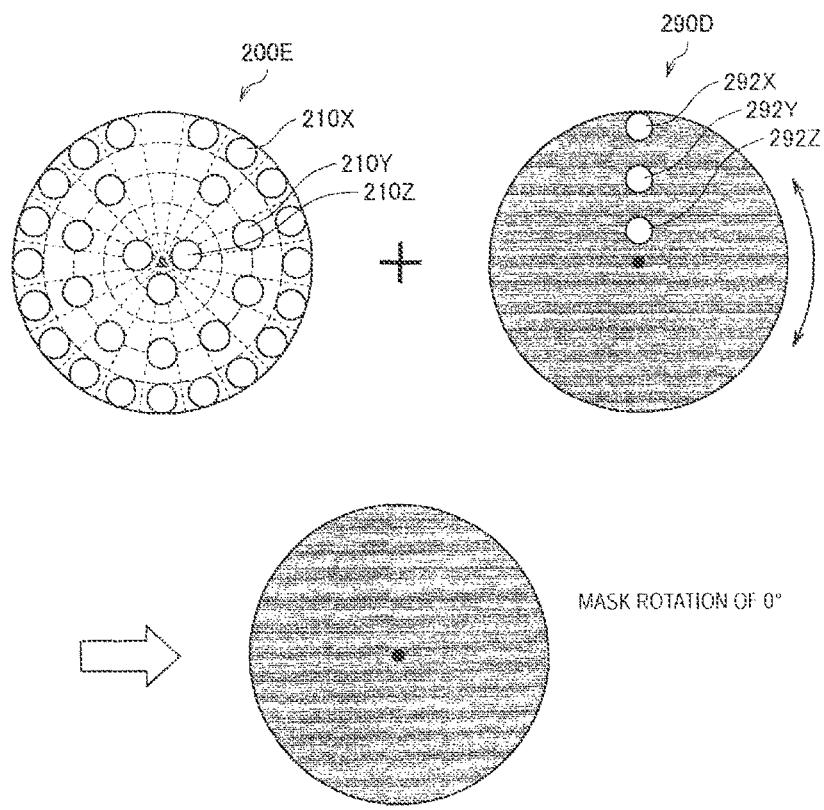

CARTRIDGE FOR PERFUMING DEVICE AND PERFUMING DEVICE

CROSS-REFERENCE TO RELATED APPLICATIONS

The present application claims the benefit of International Application No. PCT/JP2015/079942, filed Oct. 23, 2015, which claims priority to U.S. Provisional Application No. 62/130,217, filed Mar. 9, 2015, the disclosures of which are incorporated herein by reference.

BACKGROUND

The present disclosure relates to a cartridge for a perfuming device and a perfuming device.

Perfuming devices that diffuse a fragrance by dropping a liquid fragrance material onto an ultrasonic transducer and gasifying the material or by evaporating and gasifying a fragrance material with water have been known from the past. With respect to such perfuming devices, however, a dilution ratio at the time of diffusion becomes lower easily and thus a relatively large amount of liquid fragrance material is necessary. In addition, Patent Literature 1 discloses a perfuming device which gasifies a liquid fragrance material by causing the liquid fragrance material to be adhered to porous particles and making air flow in a space filled with the porous particles.

CITATION LIST

Patent Literature

Patent Literature 1: JP 2014-67293A

SUMMARY

Technical Problem

The perfuming device disclosed in Patent Literature 1, however, is also designed to cause a liquid fragrance material to be adhered to surfaces of porous particles and thus needs a large amount of fragrance material. In addition, since the perfuming device disclosed in Patent Literature 1 causes the liquid fragrance material to be adhered to porous particles, a storage container that accommodates the porous particles is necessary, which leads to an increased size of the perfuming device.

Therefore, the present disclosure provides a novel and improved cartridge for a perfuming device and perfuming device which cause efficient perfuming using a relatively small amount of fragrance material while an increase in size of the perfuming device is minimized.

Solution to Problem

According to the present disclosure, there is provided a cartridge for a perfuming device, including: a main body part; an air flow channel that is provided in the main body part and has both ends that are open; and a fragrance material held in at least a part of an inner surface of the air flow channel.

Further, according to the present disclosure, there is provided a perfuming device including: a cartridge including a main body part, an air flow channel that is provided in the main body part and has both ends that are open, and a fragrance material held in at least a part of an inner surface of the air flow channel; and an air blowing part that supplies air to the air flow channel of the cartridge.

Advantageous Effects of Invention

According to the present disclosure described above, it is possible to efficiently perfume using a relatively small amount of fragrance material while an increase in size of a perfuming device is minimized.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 31 is an illustrative diagram showing rotation angles of the mask and opening positions of the air flow channels.

FIG. 32 is an illustrative diagram showing a state in which air flow channels are closed.

DETAILED DESCRIPTION

Figure 1:
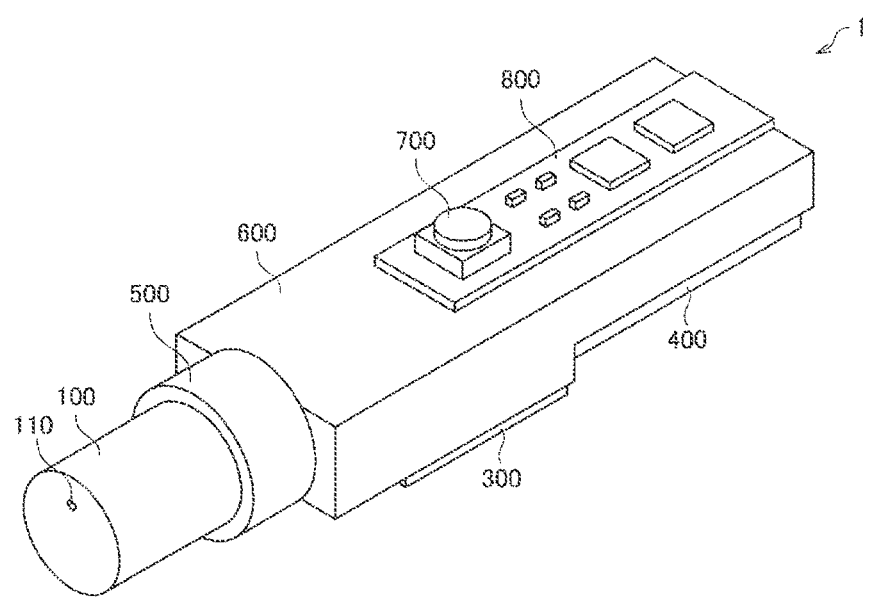
FIG. 1 is a perspective view showing an example of a perfuming device according to a first embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that description will be provided in the following order.
1. First Embodiment
1-1. Perfuming device
1-2. Fragrance cartridge
1-2-1. Overall configuration
1-2-2. Air flow channel
1-3. Modified examples
1-4. Effects
2. Second Embodiment
2-1. Basic configuration
2-2. First example
2-3. Second example
2-4. Modified example
2-5. Effects
3. Third Embodiment 1. First Embodiment 1-1. Perfuming Device First, an overall configuration example of a perfuming device 1 according to a first embodiment of the present disclosure will be described with reference to FIGS. 1 to 5.

Figure 2:
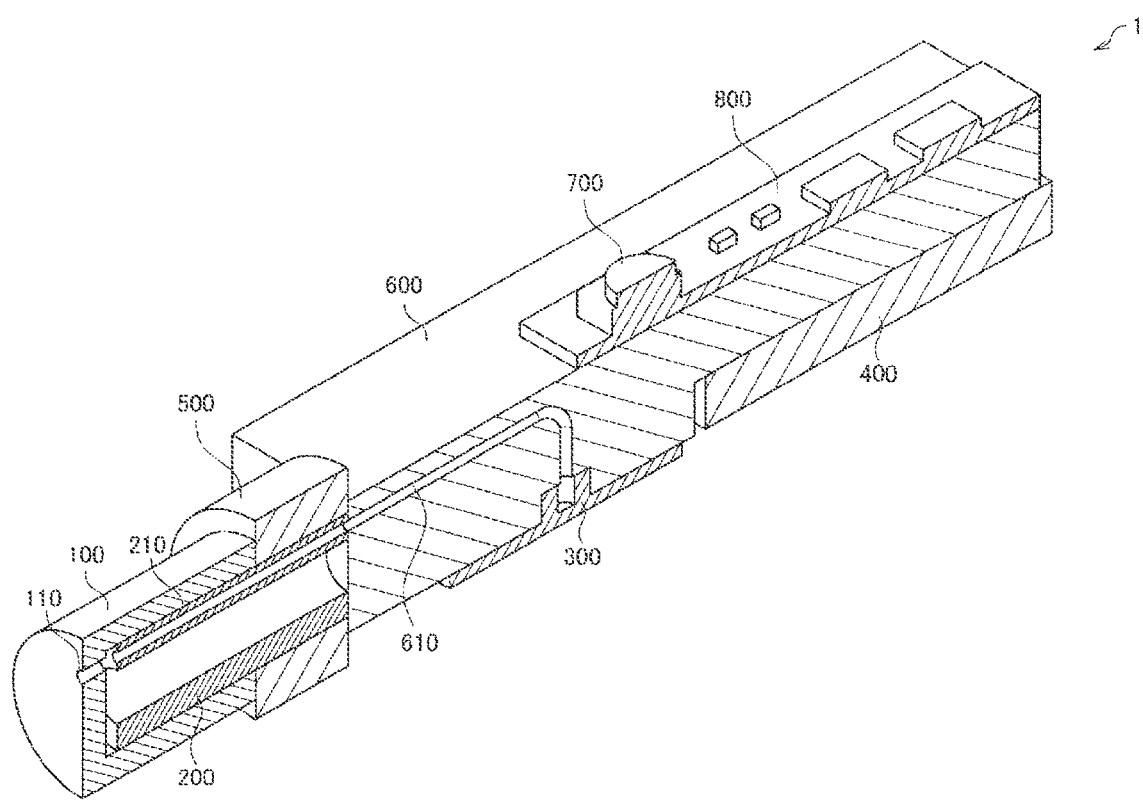
FIG. 2 is a cross-sectional view of the perfuming device according to the embodiment.
Figure 3:
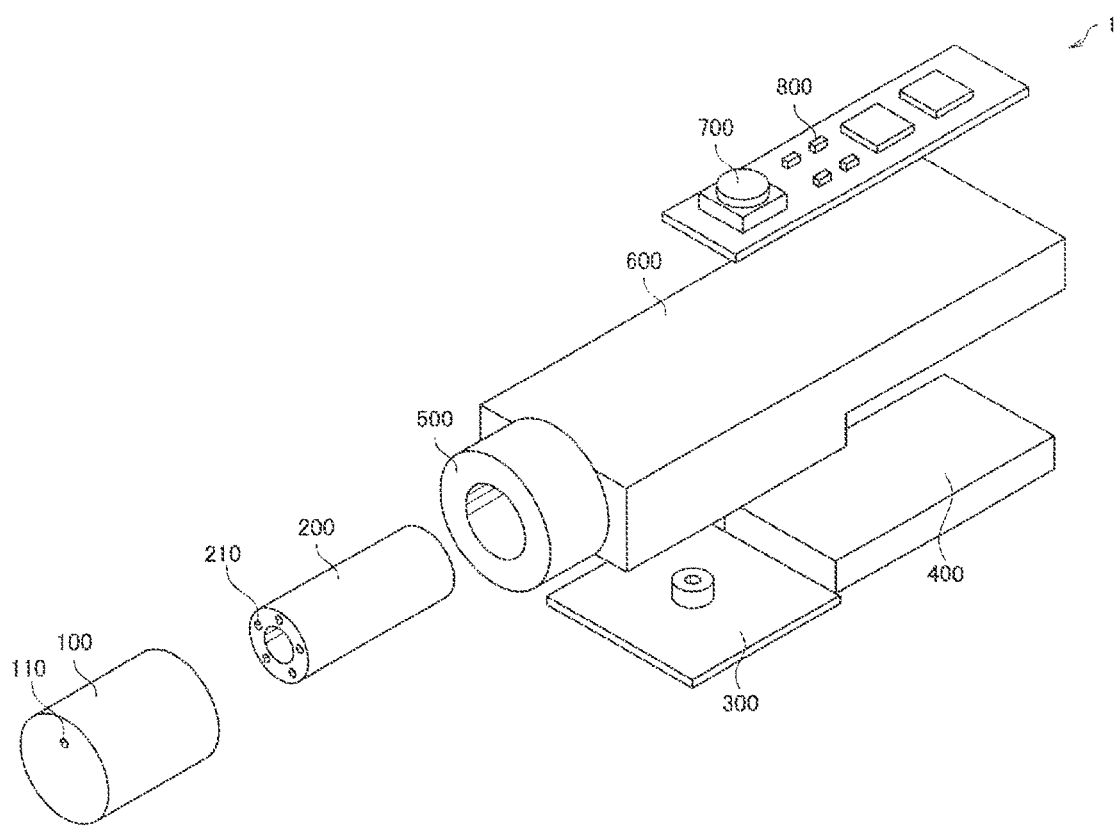
FIG. 3 is an exploded perspective view of the perfuming device according to the embodiment.

FIG. 1 is a perspective view showing the perfuming device 1, FIG. 2 is a schematic diagram showing a cross-section of the perfuming device 1, and FIG. 3 is an exploded perspective view of the perfuming device 1. The perfuming device 1 according to the present embodiment includes a lid 100, a fragrance cartridge 200, an air pump 300, a battery 400, a cartridge holding unit 500, a chassis 600, a switch 700, and a drive substrate 800. The perfuming device 1 is a device which causes air to flow in an air flow channel 210 provided in the fragrance cartridge 200 to gasify and emit a fragrance material held in the air flow channel 210. The area of the perfuming device 1 in which the chassis 600 is positioned may be contained in a housing that is not illustrated. In this case, the switch 700 is configured to be operable from outside of the housing.

The air pump 300 is an example of an air blowing part that is disposed on the chassis 600 and presses air toward the fragrance cartridge 200. In the perfuming device 1 illustrated in FIG. 2, the air pump 300 supplies air to the air flow channel 210 of the fragrance cartridge 200 via a channel 610 provided in the chassis 600. The air pump 300 may receive supply of power from the battery 400 to be driven by the power. The air pump 300 can be, for example, a diaphragm pump which sucks in and presses out air by deforming a diaphragm when an alternating current is supplied to a piezoelectric element.

Note that an air blowing part that supplies air toward the fragrance cartridge 200 is not limited to the air pump 300, and may be, for example, an air blower of a fan rotation type. In addition, an air blowing part that supplies air toward the fragrance cartridge 200 may not be an electrically operating type, and may be a manually operating type. When a means for supplying air is set to be of a manually operating type, the battery 400, the switch 700, and the drive substrate 800 may be omitted.

The battery 400 is disposed on the chassis 600 and stores power for driving the air pump 300. The battery 400 may be a primary battery that can only discharge power, or may be a secondary battery that can be charged with and discharge power. The battery 400 and the air pump 300 are electrically connected to each other with electric wiring that is not illustrated.

The drive substrate 800 is disposed on the chassis 600, and electronic components and the like including the switch 700 are installed on the drive substrate 800. The switch 700 switches electric conduction to the air pump 300 on and off. For example, electric conduction is switched on and off by repeating depressing of the switch 700, and electric conduction may be maintained in an on-state while the switch 700 is depressed. Another electronic component exemplified as a light source such as a light emitting diode (LED) which indicates an operation state of the perfuming device 1 may be installed on the drive substrate 800. In addition, a communication device may be installed on the drive substrate 800 in order to make the perfuming device 1 operable using a remote controller, a smartphone, or the like.

The fragrance cartridge 200 has at least one air flow channel 210. At least a part of an inner surface of the air flow channel 210 holds, for example, an essential oil or a liquid fragrance material obtained by diluting an essential oil in ethanol adhered thereto. By causing air supplied by the air pump 300 to flow in the air flow channel 210 of the fragrance cartridge 200, the liquid fragrance material is gasified and then emitted from the air flow channel 210 along with the air. In the perfuming device 1 according to the present embodiment, the inner diameter of the air flow channel 210 of the fragrance cartridge 200 is relatively small, and thus it is difficult for the fragrance material to be emitted to the outside in a state in which no air flows in the air flow channel 210. A configuration of the fragrance cartridge 200 will be described in more detail below.

The cartridge holding unit 500 holds the fragrance cartridge 200. In the perfuming device 1 according to the present embodiment, the inner circumference of the hollow tubular cartridge holding unit 500 holds the likewise hollow tubular fragrance cartridge 200. The fragrance cartridge 200 is held such that the air flow channel 210 can communicate with a channel 610 provided in the chassis 600. In addition, when the fragrance cartridge 200 has a plurality of air flow channels 210, for example, the cartridge holding unit 500 holding the fragrance cartridge 200 may rotate axially with respect to the chassis 600 to switch the air flow channels 210 communicating with the channel 610 of the chassis 600.

A configuration in which the air flow channels 210 of the fragrance cartridge 200 communicating with the channel 610 of the chassis 600 are switched is not limited thereto. For example, a rotatable member having a channel may be provided between the chassis 600 and the fragrance cartridge 200 and the air flow channels 210 of the fragrance cartridge 200 communicating with the channel 610 of the chassis 600 may be switched by rotating the member. Alternatively, a mask, a cap, or the like which can switch between opening and closing of the air flow channels 21 of the fragrance cartridge 200 may be used such that the mask or the like is rotated to switch an air flow channel 210 which is open.

The lid 100 is mounted on the fragrance cartridge 200 to cover the fragrance cartridge 200 held by the cartridge holding unit 500. A discharge hole 110 is provided in the lid 100 and thus air containing a gasified fragrance material component passing the air flow channels 210 of the fragrance cartridge 200 is emitted to the outside through the discharge hole 110. Although an inner diameter of the discharge hole 110 is not particularly limited, the inner diameter can be set to have at least a size greater than or equal to the inner diameter of the air flow channel 210 in order not to obstruct the flow of the air flowing in the air flow channels 210 of the fragrance cartridge 200.

Note that, although not illustrated, the perfuming device 1 may include an appropriate valve device, a shutter device, a sealing device, or other arbitrary shielding device at an end face of the fragrance cartridge 200 or an end part of the air flow channels 210 so that the air flow channels 210 can be maintained in a shielded state when it is not used.

Figure 4:
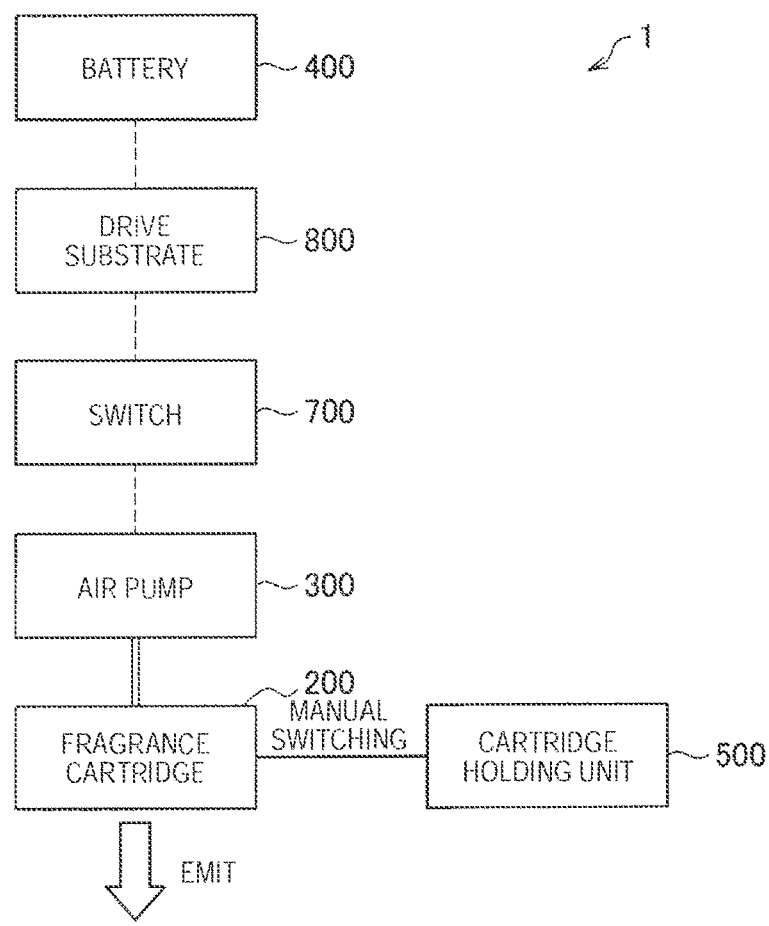
FIG. 4 is a block diagram showing a configuration example of the perfuming device according to the embodiment.

FIG. 4 shows an example of a system block diagram of the perfuming device 1. The battery 400 is electrically connected to the air pump 300 via the drive substrate 800 and the switch 700. The power of the battery 400 is supplied to the air pump 300 in accordance with an operation of the switch 700. When the air pump 300 is driven and thus air flows into the air flow channels 210 of the fragrance cartridge 200, the fragrance material held in an inner surface of the air flow channels 210 is gasified and thus a fragrance is emitted along with the air. In addition, in the example of FIG. 4, the cartridge holding unit 500 is rotated manually, and thus the air flow channels 210 of the fragrance cartridge 200 to which air supplied from the air pump 300 is introduced can be switched between.

Figure 5:
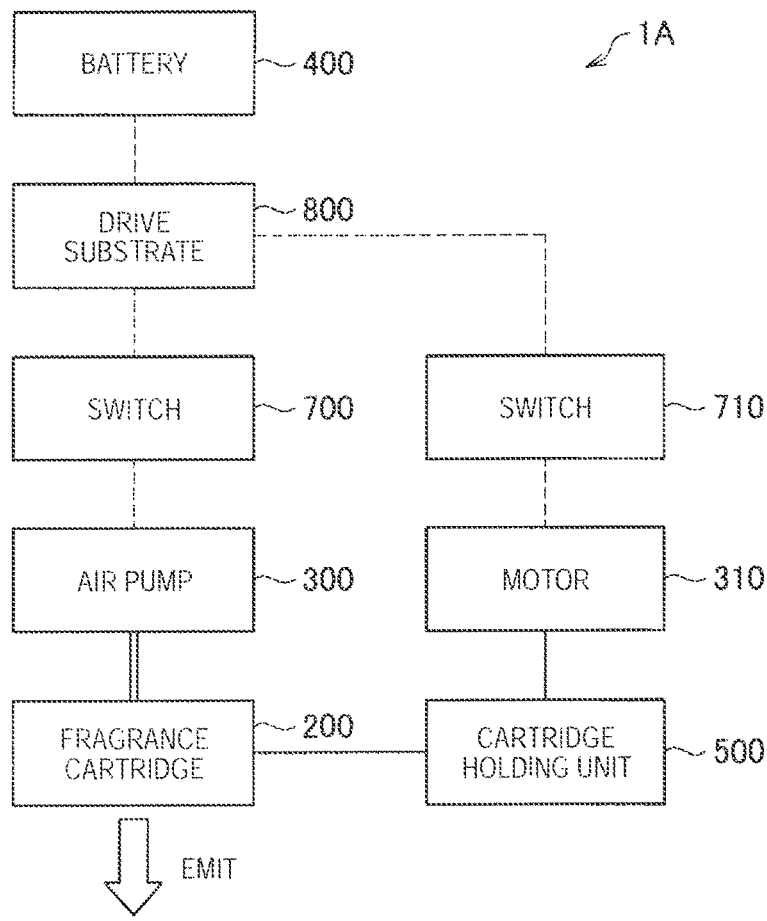
FIG. 5 is a block diagram showing another configuration example of a perfuming device according to the embodiment.

FIG. 5 shows another example of a system block diagram of a perfuming device 1A. In the example shown in FIG. 5, the cartridge holding unit 500 is rotated by a motor 310 and thus the air flow channels 210 of the fragrance cartridge 200 to which air supplied from the air pump 300 is introduced can be switched between.

The perfuming device 1 can be used as, for example, a device which diffuses a fragrance over a relatively extensive space. In addition, the perfuming device 1 can be used as a device which emits a fragrance over a limited range, unlike perfuming devices of the past. The perfuming device can be used by a user, for example, to cause a fragrance to be emitted close to his or her face once or a plurality of times to feel relaxation. Since the fragrance is not diffused over a wide range in that case, it is difficult for nearby people to detect the fragrance.

1-2. Fragrance Cartridge 1-2-1. Overall Configuration

Figure 6:
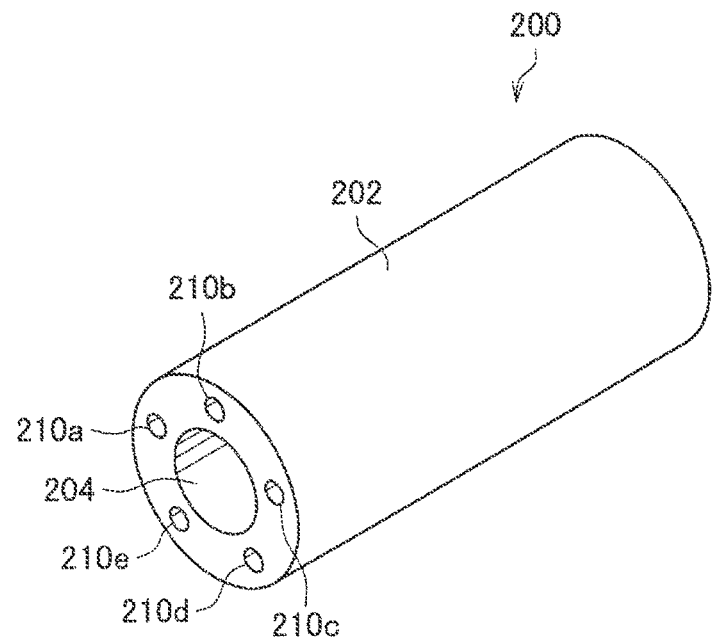
FIG. 6 is a perspective view showing an example of a fragrance cartridge according to the embodiment.

A configuration of the fragrance cartridge 200 will be described below in detail. FIG. 6 is a perspective view showing an example of the fragrance cartridge 200. The fragrance cartridge 200 is an example of a cartridge that includes a plurality of air flow channels 210a to 210e and can be used with air flow channels in which air flows being switched between while being installed in the perfuming device 1.

The fragrance cartridge 200 includes a main body part 202, an axial hole 204, and the plurality of air flow channels 210a to 210e. The main body part 202 has a tubular outer shape. The main body part 202 has the axial hole 204, and the outer circumferential surface of the main body part 202 and the inner circumferential surface of the axial hole 204 form concentric circles. The axial hole 204 can be used as, for example, a guide at the time of installation in the cartridge holding unit 500 or the perfuming device 1. Note that an outer shape of the fragrance cartridge 200 is not limited to a tubular shape as long as a shape enables the fragrance cartridge to be mounted in the perfuming device 1 and the air flow channels 210 to communicate with the channel through which air is supplied. An outer shape of the fragrance cartridge 200 can be, for example, a cylinder, a rectangular parallelepiped, a cuboid, or other appropriate shapes.

The air flow channels 210a to 210e are formed in the main body part 202 in the axis line direction. The air flow channels 210a to 210e are disposed at equal intervals on a circumference having the axis center of the fragrance cartridge 200 as the center. Accordingly, for example, by rotating the fragrance cartridge 200 illustrated in FIG. 6 around the axis by a given rotation angle, the air flow channels 210a to 210e in which air flows can be switched between.

Figure 7:
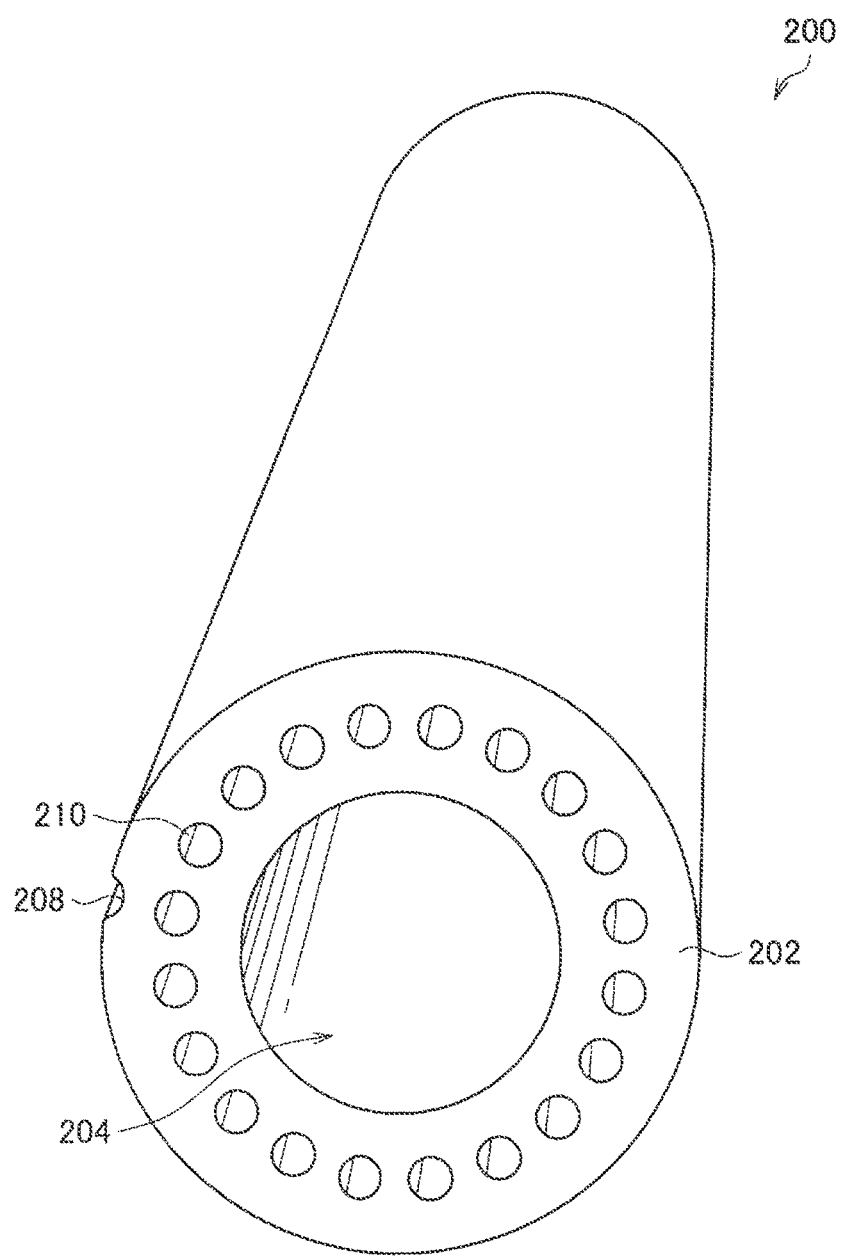
FIG. 7 is a perspective view showing a configuration example of the fragrance cartridge according to the embodiment.

The number of air flow channels 210 provided in the main body part 202 is not limited to 5. For example, more air flow channels 210 may be provided as illustrated in FIG. 7. Also in this case, by disposing the plurality of air flow channels 210 on a circumference having the axis center of the fragrance cartridge 200 as a center and rotating the fragrance cartridge 200 around the axis, the air flow channels 210 in which air flows can be switched between. In addition, only one air flow channel 210 may be provided in the main body part 202. In this case, a configuration for switching the air flow channels 210 in which air flows therein may be omitted from the perfuming device 1.

Furthermore, an engagement groove 208 may be provided on the outer circumferential surface of the fragrance cartridge 200 as illustrated in FIG. 7. For example, an engagement projection in a size in which the engagement projection can be disposed in the engagement groove 208 may be provided on an inner circumferential surface of the cartridge holding unit 500 illustrated in FIG. 2 and the like, and the fragrance cartridge 200 may be mounted in the cartridge holding unit 500 such that the engagement projection fits into the engagement groove 208. Accordingly, relative positioning between the cartridge holding unit 500 and the fragrance cartridge 200 is possible. In addition, since relative rotation between the cartridge holding unit 500 and the fragrance cartridge 200 is not possible, the fragrance cartridge 200 can be rotated by rotating the cartridge holding unit 500.

As constituent materials of the fragrance cartridge 200, for example, one kind or a plurality of kinds of material among a polymeric resin such as an acrylic resin, a urethane resin, an ABS resin, a polyetheretherketone (PEEK) resin, a polyacetal (POM) resin, a silicone resin, a fluorine resin, a cycloolefin polymer resin, or a polyimide resin, a metal such as stainless steel or aluminum, an inorganic crystalline material such as quartz, and glass can be used. However, a constituent material of the fragrance cartridge 200 is not limited thereto. Note that the fragrance cartridge 200 can be manufactured using a 3D printer, and a material suitable for a 3D printer may be selected as a constituent material of the fragrance cartridge 200.

1-2-2. Air Flow Channel

Next, the air flow channels 210 formed in the fragrance cartridge 200 will be described.
(1-2-2-1. Basic Configuration)

The fragrance cartridge 200 according to the present embodiment can have, for example, air flow channels 210 with an inner diameter of 10 to 3,000 μm. In particular, a channel with an inner diameter of dozens to hundreds of μm can also be called a "micro channel." The air flow channels 210 with this inner diameter holds a liquid fragrance material adhered to the inner surface, and thus a small amount of a fragrance material can be stably held therein. Thus, it is not necessary to add the fragrance material dropwise each time it is used. The inner diameter of each air flow channel 210 may be a value in the range of 50 to 500 μm, or a value in the range of 100 to 200 μm.

In addition, since the fragrance cartridge 200 has the air flow channels 210 with a relatively small inner diameter, the outlet opening is small and thus a flux of diffusion when fragrance is emitted can be narrowed. Thus, fragrance can be emitted over a limited range so that, for example, a user can enjoy the fragrance for his or her private use.

Further, if the air flow channels 210 have a relatively small inner diameter, a high ratio of a surface area of the air flow channel 210 to a volume thereof can be secured, and thus a small amount of fragrance material can be gasified at a high concentration and can be emitted along with air. Furthermore, if the air flow channels 210 have a relatively small inner diameter, an outer size of the fragrance cartridge 200 can be reduced not only when only one air flow channel 210 is formed but also when a plurality of air flow channels 210 are formed, which results in the fragrance cartridge 200 being able to be carried easily and also the perfuming device 1 being able to be carried easily.

The air flow channels 210 may be provided in the main body part 202 in a linear shape or a curved shape. Alternatively, the air flow channels 210 may partly include a linear part and a curved part. By forming the air flow channels 210 in a curved shape, a length of the air flow channels 210 in the main body part 202 can be long and thus an amount of held fragrance materials can be increased.

An orientation of the outlet opening of the air flow channels 210 may be parallel with, perpendicular to, or have an arbitrary angle with respect to the axial direction of the main body part 202. In addition, a cross-section shape of the air flow channels 210 is not particularly limited as long as the shape enables liquid fragrance materials to be adhered to and held in an inner surface thereof and air to flow in the air flow channels 210. A cross-section shape of the air flow channels 210 can be, for example, a circular shape, an oval shape, a quadrangular shape, a rectangular shape, or other appropriate shapes.

Figure 8:
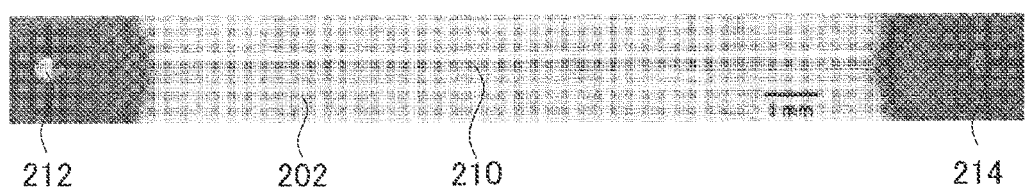
FIG. 8 is an illustrative diagram showing an air flow channel of the fragrance cartridge.

FIG. 8 is an image captured viewed through an air flow channel 210 formed in the fragrance cartridge 200. The air flow channel 210 shown in FIG. 8 is a channel having a quadrangular cross-section of 100 μm square, and a cross-sectional area of an inlet opening 214 and an outlet opening 212 at both ends is larger than the center part. A liquid fragrance material is adhered to and held in the inner surface of the air flow channel 210. A volume of the air flow channel 210 is about 0.18 μL. For example, when 0.25 μL of a liquid fragrance material is injected from one end side of the air flow channel 210 and then air is supplied to the air flow channel 210, a surplus of the fragrance material is discharged and only the fragrance material adhered to the inside is held in the inner surface of the air flow channel 210.

In addition, one or plural air flow channels 210 may be formed in the fragrance cartridge 200. If the fragrance cartridge 200 has a plurality of air flow channels 210, a total amount of fragrance materials held in the fragrance cartridge 200 can be higher. Thus, when fragrance materials held therein are all the same, it is possible to lengthen a time over which one fragrance cartridge 200 can be used. In addition, if a plurality of air flow channels 210 are formed, a plurality of different fragrance materials can be held, and different kinds of fragrance can be emitted by switching between the air flow channels 210 in which air flows.
(1-2-2-2. Tapered Shape)

Figure 9:
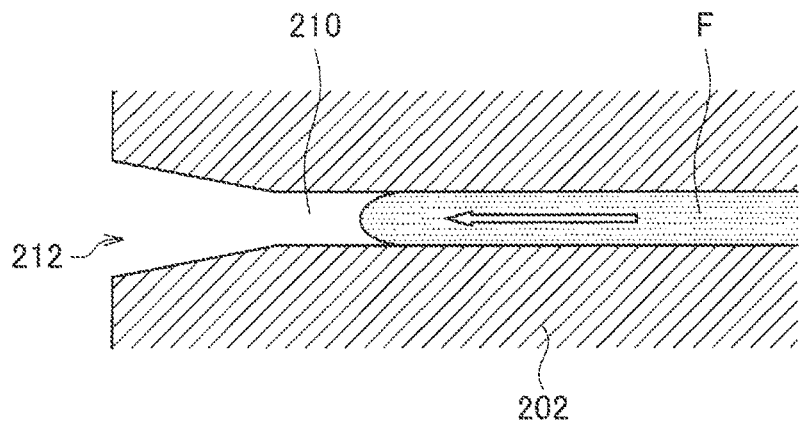
FIG. 9 is a cross-sectional view showing an outlet opening of the air flow channel.
Figure 10:
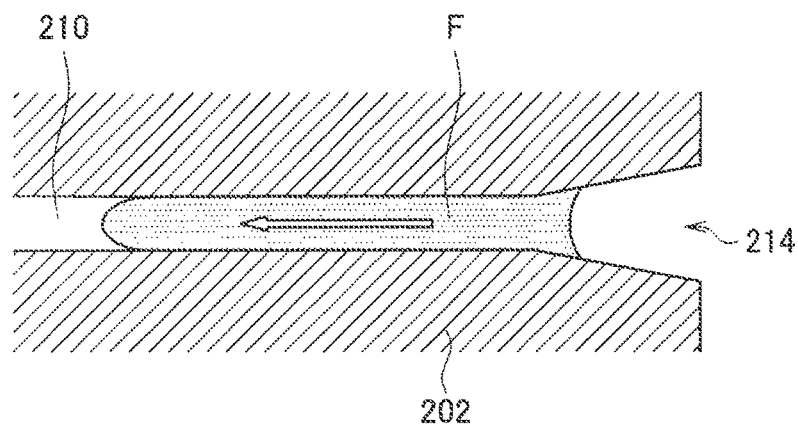
FIG. 10 is a cross-sectional view showing an inlet opening of the air flow channel.
Figure 11:
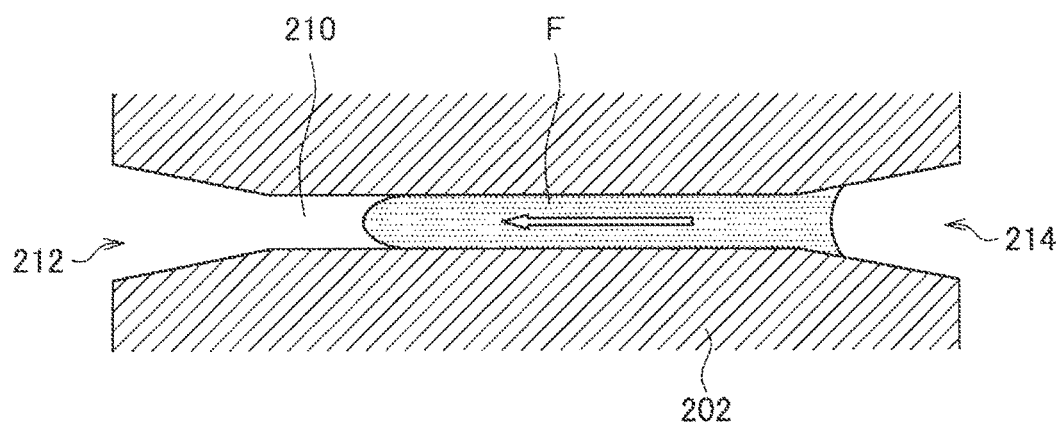
FIG. 11 is a cross-sectional view showing the inlet opening and the outlet opening of the air flow channel.

FIGS. 9 to 11 are illustrative diagrams of the air flow channel 210 in a tapered shape, showing partial cross-sectional views of the air flow channel 210 formed in the main body part 202. As illustrated in FIG. 9, the outlet opening 212 of the air flow channel 210 may have a tapered shape in which a diameter increases toward an opening end. If the outlet opening 212 has a tapered shape, a fragrance material F emitted from the air flow channel 210 is easily diffused. In addition, as illustrated in FIG. 10, the inlet opening 214 of the air flow channel 210 may have a tapered shape in which a diameter increases toward an opening end. If the inlet opening 214 has a tapered shape, a small amount of a liquid fragrance material F can be easily injected into the air flow channel 210, which prevents the fragrance material F from being adhered to and remaining around an end part of the inlet opening 214.

The outlet opening 212 or the inlet opening 214 may have a tapering angle with respect to the center axis of the air flow channel 210 in the range of 5° to 45°, or the range of 10° to 30°. In addition, an inner diameter of the outlet opening 212 or the inlet opening 214 having a tapered shape may be set to be, for example, a value in the range of 30 to 2,000 μm, a value in the range of 50 to 500 μm, or a value in the range of 100 to 300 μm. Note that, as illustrated in FIG. 11, the inlet opening 214 and the outlet opening 212 of the air flow channel 210 may have tapered shapes in which diameters expand toward the opening ends.

(1-2-2-3. Branching Section and Merging Section)

Figure 12:
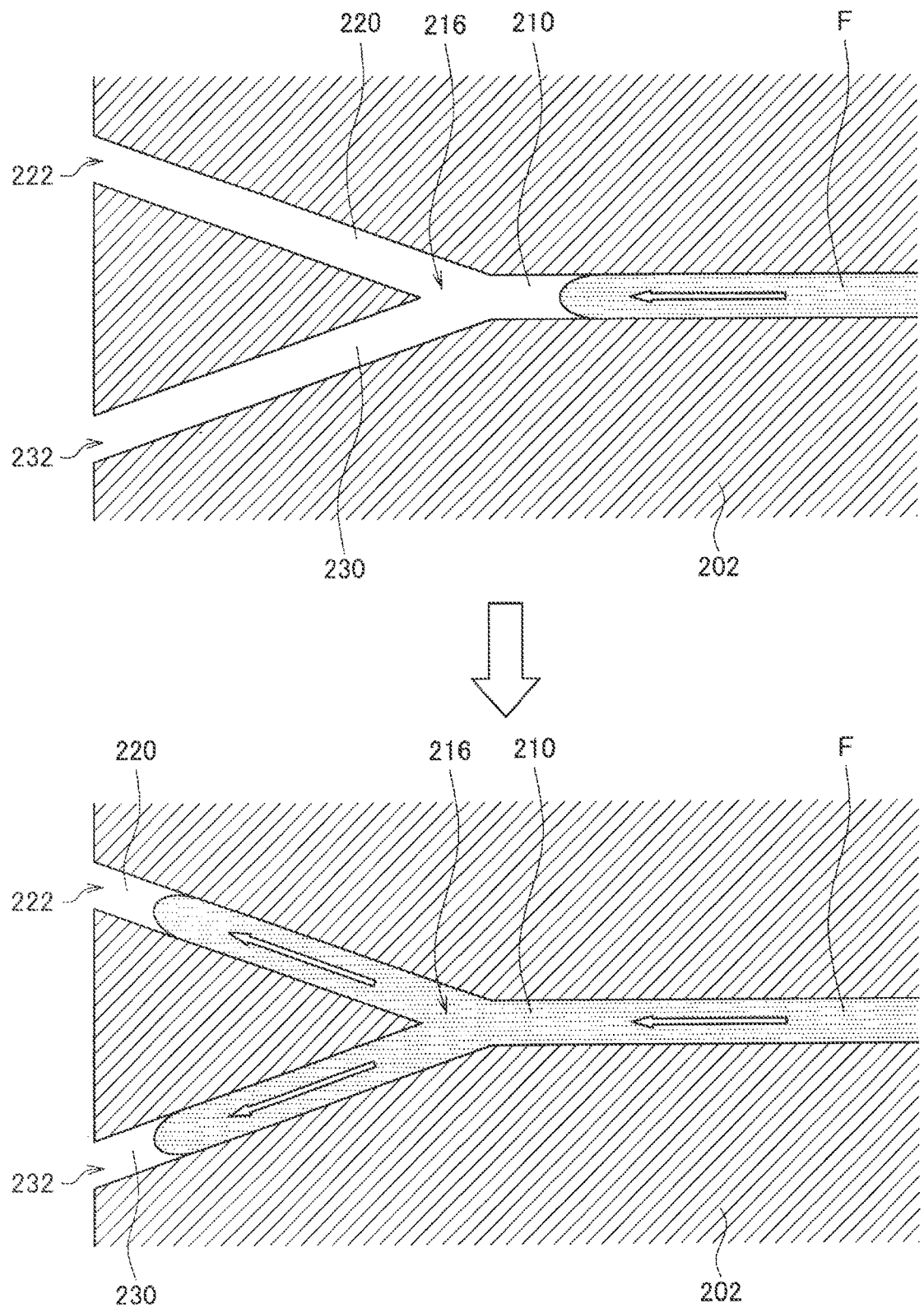
FIG. 12 is a cross-sectional view showing the air flow channel having a branching section on the outlet opening side.
Figure 13:
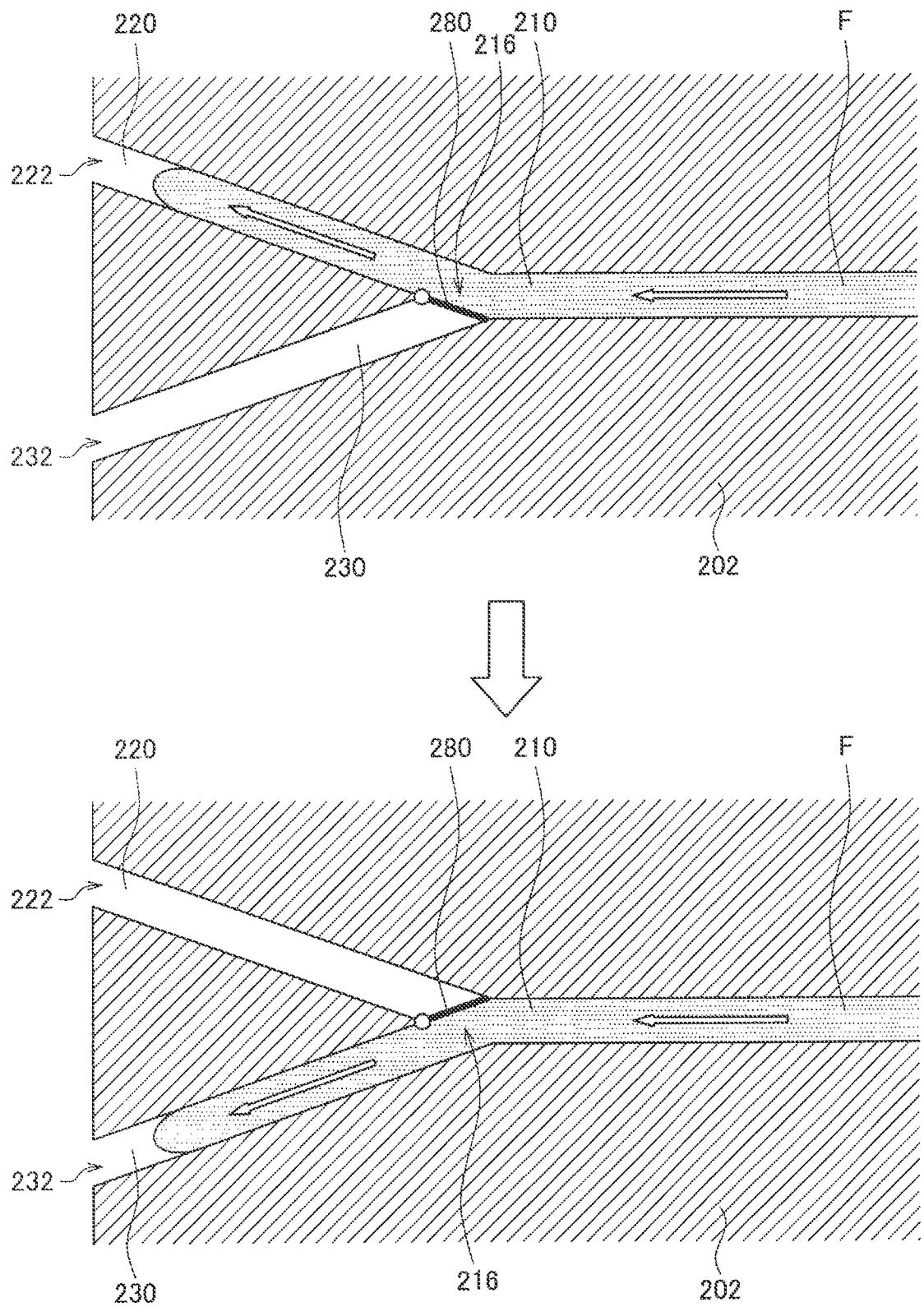
FIG. 13 is a cross-sectional view showing the outlet opening of the air flow channel of which a valve device is provided in the branching section.
Figure 14:
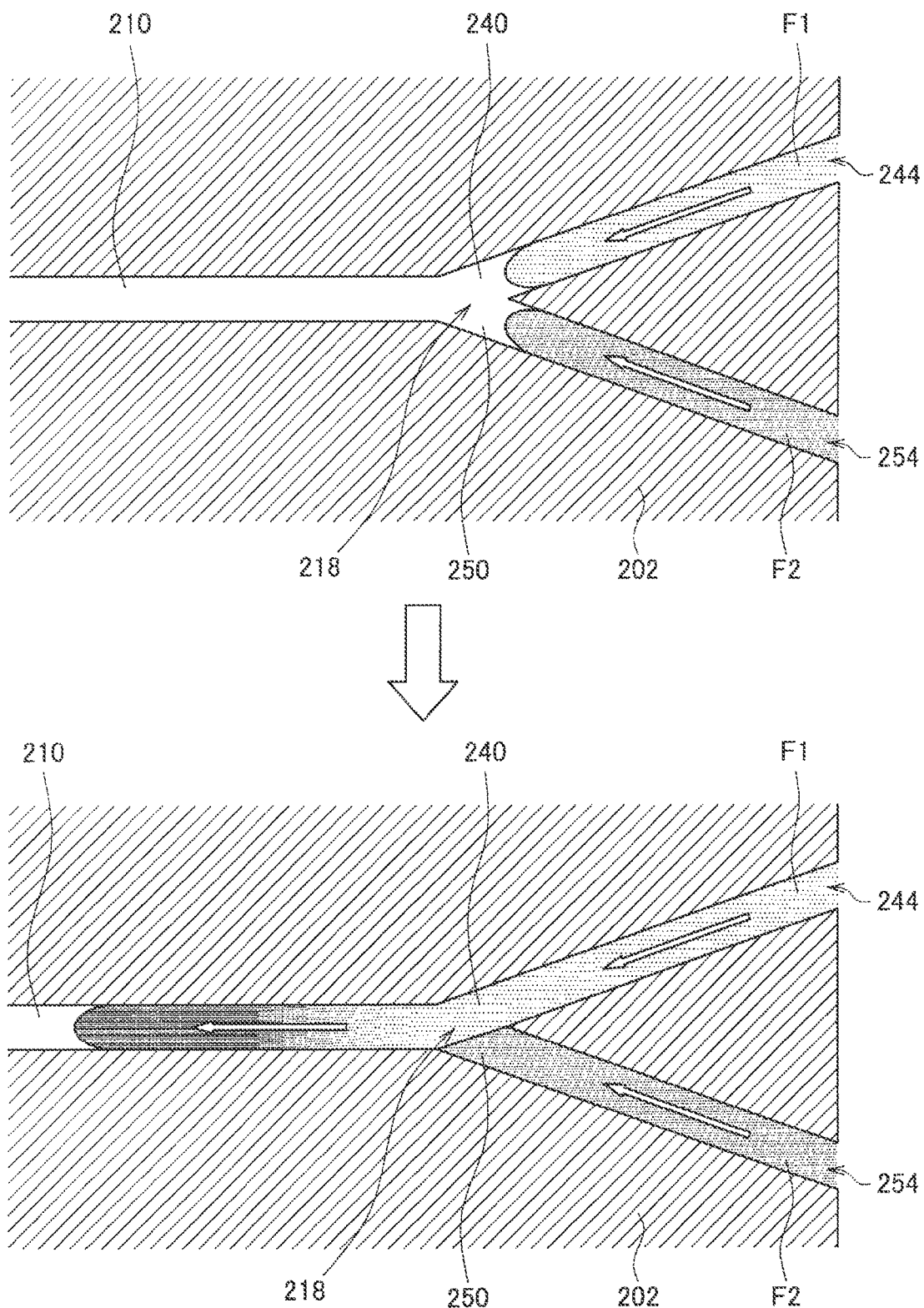
FIG. 14 is a cross-sectional view showing the air flow channel having a merging section on the inlet opening side.

FIG. 12 to FIG. 14 are illustrative diagrams of the air flow channel 210 having a branching section or a merging section, showing partial cross-sectional views of the air flow channel 210 formed in the main body part 202. As illustrated in FIG. 12, the air flow channel 210 may have a branching section 216, and may branch into a plurality of branch channels 220 and 230. In this case, the air flow channel 210 has a plurality of outlet openings 222 and 232. As the air flow channel 210 branches at the branching section 216, thereby having the plurality of outlet openings 222 and 232, a fragrance material F can be emitted in a plurality of difference directions. Even when the air flow channel 210 has the branching section 216, the liquid fragrance material F can be injected from an inlet opening side of the air flow channel 210 and thus the fragrance material F can spread into each of the two branch channels 220 and 230. In addition, by supplying air from the inlet opening side thereafter, a surplus of the fragrance material F can be discharged, and the fragrance material F can be adhered to and held in the inner surface of the air flow channel 210 including the branch channels 220 and 230.

Note that the number of branching sections at which a plurality of branch channels are formed toward the outlet opening side of the air flow channel 210 is not limited to one and may be plural.

Furthermore, as illustrated in FIG. 13, a valve device 280 or a gate device for switching a flow of the fragrance material F or air flowing inside the air flow channel 210 may be provided at the branching section 216. By providing the valve device 280 in the branching section 216, a channel in which air flows can be switched between one branch channel 220 and the other branch channel 230, and thus a direction in which the fragrance material F is emitted can be selected. In addition, by providing the valve device 280 in the branching section 216, the fragrance material F can be held in one branch channel 220 separately from the fragrance material F held in the other branch channel 230 when a liquid fragrance material F is held in the air flow channel 210.

The valve device 280 can be constituted by, for example, a flap that is formed of a magnetic material and can rotate using a vertex of the branching section 216 as a rotation axis and an actuator that generates a magnetic field with electric conduction at any one side of the branch channels 220 and 230 (the upper side or the lower side of FIG. 13). The flap can be pulled when electric conduction to the actuator is turned on or off in the valve device 280 and thereby it is possible to switch which of the branch channels 220 and 230 is blocked by the flap.

In addition, as illustrated in FIG. 14, the air flow channel 210 may have a plurality of inlet openings 244 and 254 and a plurality of branch channels 240 and 250 may merge at a merging section 218. Since the air flow channel 210 has the plurality of inlet openings 244 and 254 and the branch channels merge at the merging section 218, for example, the branch channels 240 and 250 can hold different fragrance materials F1 and F2, and by selecting the inlet openings 24 and 254 into which air is introduced, the fragrance materials F1 and F2 to be emitted from the air flow channel 210 can be switched between. In addition, by introducing air from the two inlet openings 244 and 254, the two fragrance materials F1 and F2 can be mixed and emitted.

Furthermore, a valve device not illustrated may be provided at the merging section 218. By providing a valve device at the merging section 218, it is possible to select the fragrance material F1 or F2 to be emitted from the air flow channel 210 using the valve device, rather than selecting the inlet opening 244 or 254 into which air is introduced. Alternatively, by adjusting a rate of opening of the branch channels 240 and 250 with the valve device, a mixing rate of the fragrance materials F1 and F2 each held in the branch channels 240 and 250 can be adjusted and thus a desired fragrance material can be emitted. The valve device provided in the merging section 218 can be configured similarly to the valve device 280 provided at the above-described branching section 216.

When a gate device is used instead of the valve device 280, the gate device can have, for example, a shutter structure in which a shutter can be moved forward or backward by an arbitrary actuator and open or close the branch channels 240 and 250 respectively.

(1-2-2-4. Surface Enlarging Part)

Figure 15:
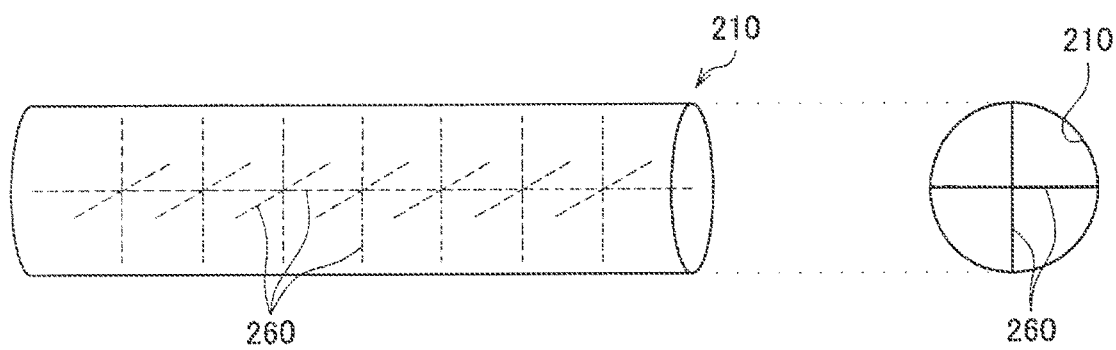
FIG. 15 is an illustrative diagram showing surface enlarging parts.
Figure 16:
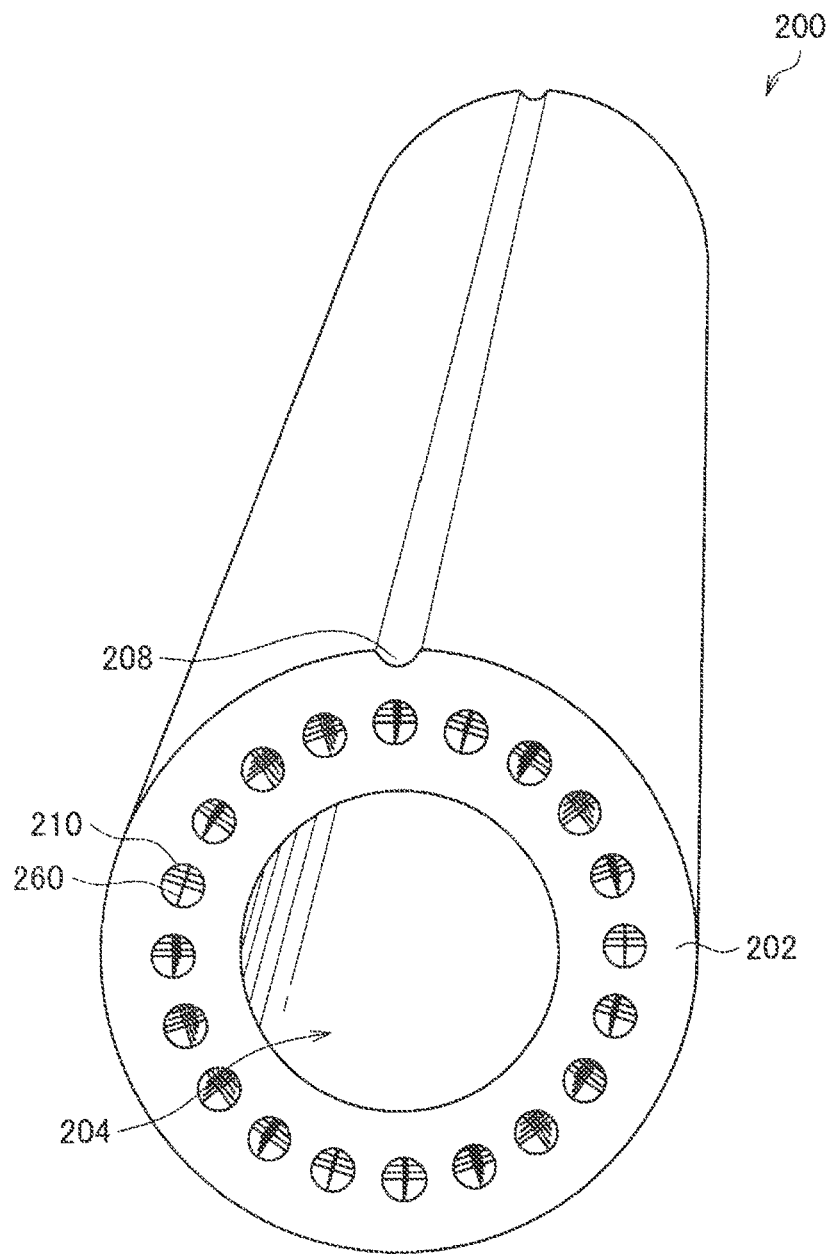
FIG. 16 is a perspective view showing a fragrance cartridge including the air flow channels with the surface enlarging parts.
Figure 17:
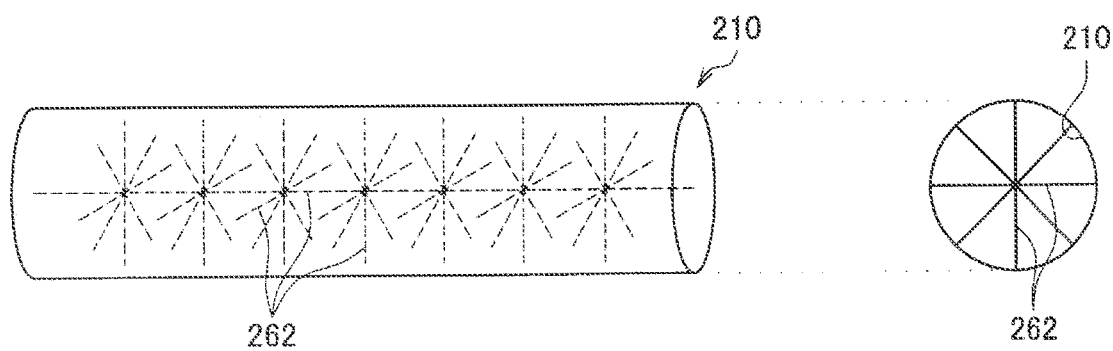
FIG. 17 is an illustrative diagram showing another example of surface enlarging parts.
Figure 18:
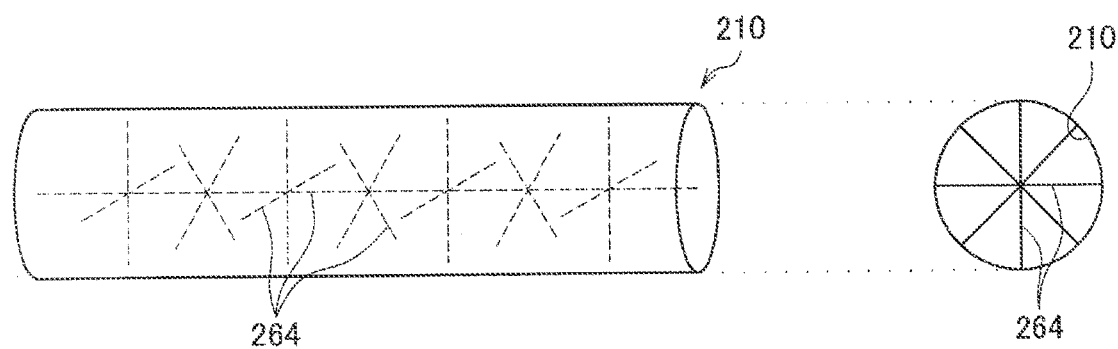
FIG. 18 is an illustrative diagram showing still another example of surface enlarging parts.

FIG. 15 to FIG. 18 are illustrative diagrams of the air flow channels 210 having surface enlarging parts, FIGS. 15, 17, and 18 are schematic diagrams showing the air flow channel 21, and FIG. 16 is an illustrative diagram showing the fragrance cartridge 200 including the air flow channels 210 with surface enlarging parts 260. As illustrated in FIGS. 15 and 16, each air flow channel 210 may include surface enlarging parts 260 which enlarge a surface inside the channel. By providing the surface enlarging parts 260 in the air flow channel 210, an area to which liquid fragrance materials adhere can be enlarged and a total amount of held fragrance materials can increase. Thus, it is possible to lengthen a total amount of time in which air can be caused to flow in one air flow channel 210 and fragrance can be emitted.

The air flow channel 210 illustrated in FIG. 15 includes the surface enlarging parts 260 formed by connecting a plurality of cross-shaped constituent parts formed on cross-sections that are perpendicular to the axis line of the air flow channel 210 at intersections of the crosses in the axial direction. By manufacturing the fragrance cartridge 200 using a 3D printer, for example, it is possible to form such surface enlarging parts 260 inside the air flow channel 210 even if the air flow channel 210 is relatively small. The surface enlarging parts 260 are disposed to be rotation-symmetric with respect to the axial center of the air flow channel 210. In addition, the surface enlarging parts 260 are disposed to be translation-symmetric in the axial direction of the air flow channel 210. Furthermore, the surface enlarging parts 260 are disposed to be reflection-symmetric with respect to an arbitrary axis.

The surface enlarging parts formed inside the air flow channel 210 may have any of various forms. For example, surface enlarging parts 262 in which a plurality of constituent elements that are formed on cross-sections that are perpendicular to the axis line of the air flow channel 210 in which four straight lines intersect are connected at intersections in the axial direction may be possible as illustrated in FIG. 17. In addition, as illustrated in FIG. 18, surface enlarging parts 264 in which a plurality of cross-shaped constituent elements that are formed on cross-sections that are perpendicular to the axis line of the air flow channel 210 are connected in the axial direction in a state in which, for example, every other surface enlarging part is rotated by 45° on the cross-sections may be possible. The surface enlarging parts 264 have the same shape as the surface enlarging parts 262 illustrated in FIG. 17 when the surface enlarging parts 264 are projected in the axial direction of the air flow channel 210.

The surface enlarging parts 262 and 264 are also disposed to be rotation-symmetric with respect to the axial center of the air flow channel 210, translation-symmetric in the axial direction of the air flow channel 210, and reflection-symmetric with respect to an arbitrary axis. In addition, the surface enlarging parts 260, 262, and 264 exemplified in FIGS. 15 to 18 are formed in a grid shape all having an arbitrary inter-axis angle and unit sides with arbitrary lengths. In other words, the surface enlarging parts 260, 262, and 264 are configured by combining a plurality of unit lattices formed by one unit side extending in a radial direction from the axis center of the air flow channel 210, the other unit side formed by rotating the one unit side a predetermined angle (90° or 45°), and an inner surface of the air flow channel 210. Thus, a fragrance material can be held at a uniform density in the air flow channel 210.

The surface enlarging parts 260, 262, and 264 can enlarge an area of the inner surface of the air flow channel 210 while maintaining the space through which air passes in order not to obstruct a flux. Thus, it is possible to increase an amount of a fragrance material held in the air flow channel 210 when a liquid fragrance material adheres to surfaces despite a gravitational force or an air flow due to a wetting property, surface tension, or a chemical interaction on an interface.

Note that it is not necessary for the surface enlarging parts to be rotation-symmetric, translation-symmetric, or reflection symmetric. In addition, it is not necessary for the surface enlarging parts to be configured with a combination of unit lattices. The surface enlarging parts can have any form as long as they can be formed not to obstruct an air flow.

(1-2-2-5. Form to Improve Straight Flow)

Figure 19:
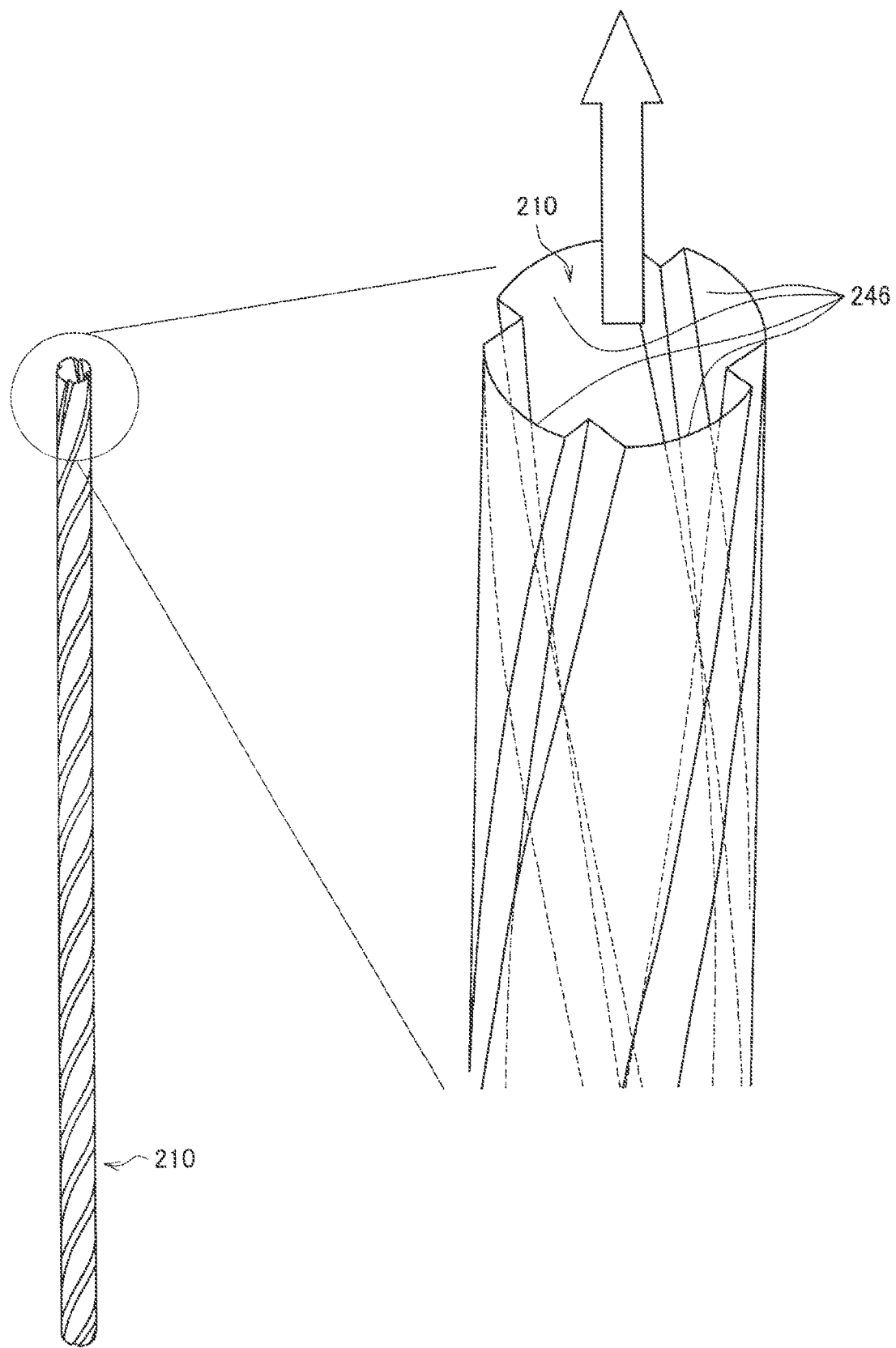
FIG. 19 is an illustrative diagram showing an air flow channel having spiral grooves on an inner circumferential surface.
Figure 20:
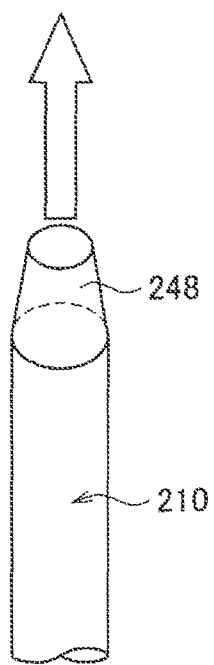
FIG. 20 is an illustrative diagram showing the air flow channel having a diameter-reducing tapered part in the outlet opening.

FIGS. 19 and 20 are schematic diagrams showing the air flow channel 210 that can improve a straight flow of emitted air. When the perfuming device 1 is used as a device which provides a private fragrance, a straight flow of an emitted fragrance may be improved so that the emitted fragrance is not diffused over a wide range. For example, the air flow channel 210 may have spiral grooves 246 in its inner circumferential surface as illustrated in FIG. 19. Since the air flow channel 210 has the spiral grooves 246, a straight flow of air flowing and being emitted from the air flow channel 210 can be improved due to a gyroscopic effect.

Alternatively, a tapered part 248 whose diameter reduces toward an opening end may be provided in an outlet opening of the air flow channel 210 as illustrated in FIG. 20. Since the tapered part 248 is provided in the outlet opening of the air flow channel 210, a flux of emitted air increases and thus a straight flow thereof can be improved.

By emitting a fragrance from the air flow channel 210 having the spiral grooves 246 or the tapered part 248 in a short period of time, the fragrance is emitted over a narrow range in which a user can feel it for himself or herself, which can realize usage of the perfuming device 1 for private use.

1-3. Modified Examples

The configuration example of the fragrance cartridge 200 according to the embodiment has been described above. The fragrance cartridge 200 according to the embodiment can be variously modified. Modified examples of the fragrance cartridge according to the embodiment will be described below.

1-3-1. First Modified Example

Figure 21:
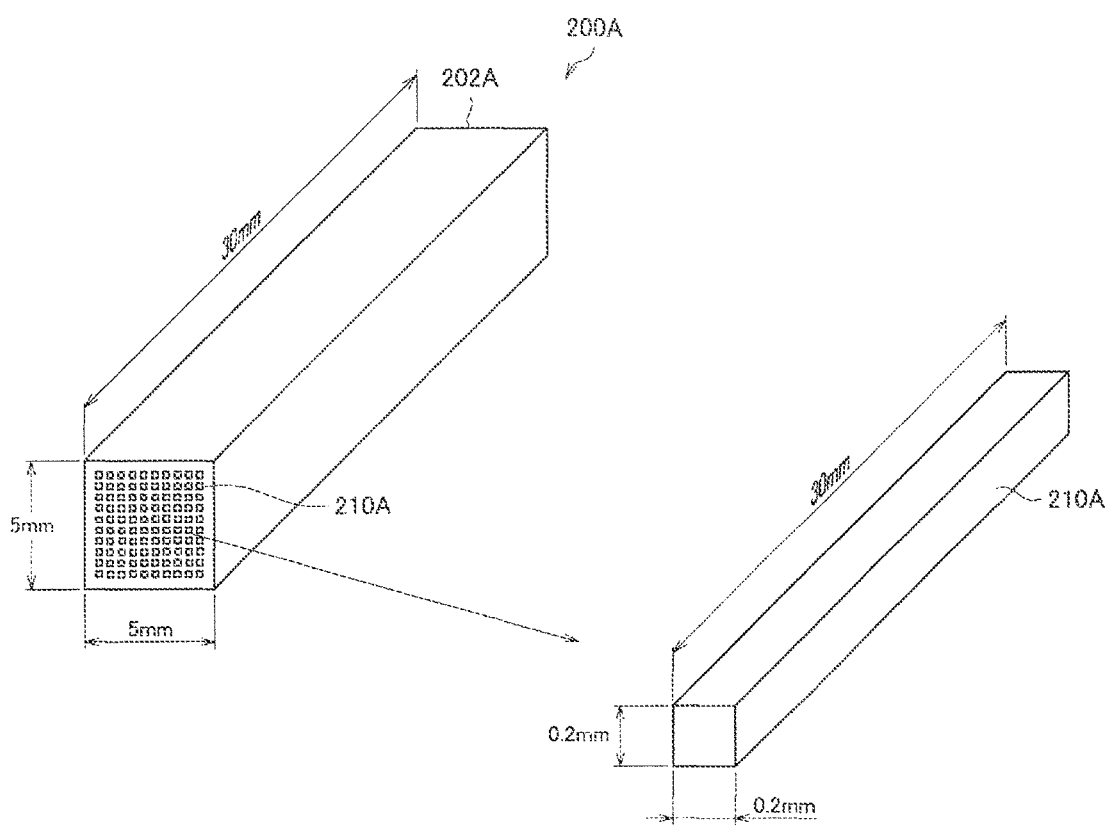
FIG. 21 is a perspective view showing a fragrance cartridge and air flow channels according to a first modified example of the embodiment.
Figure 22:
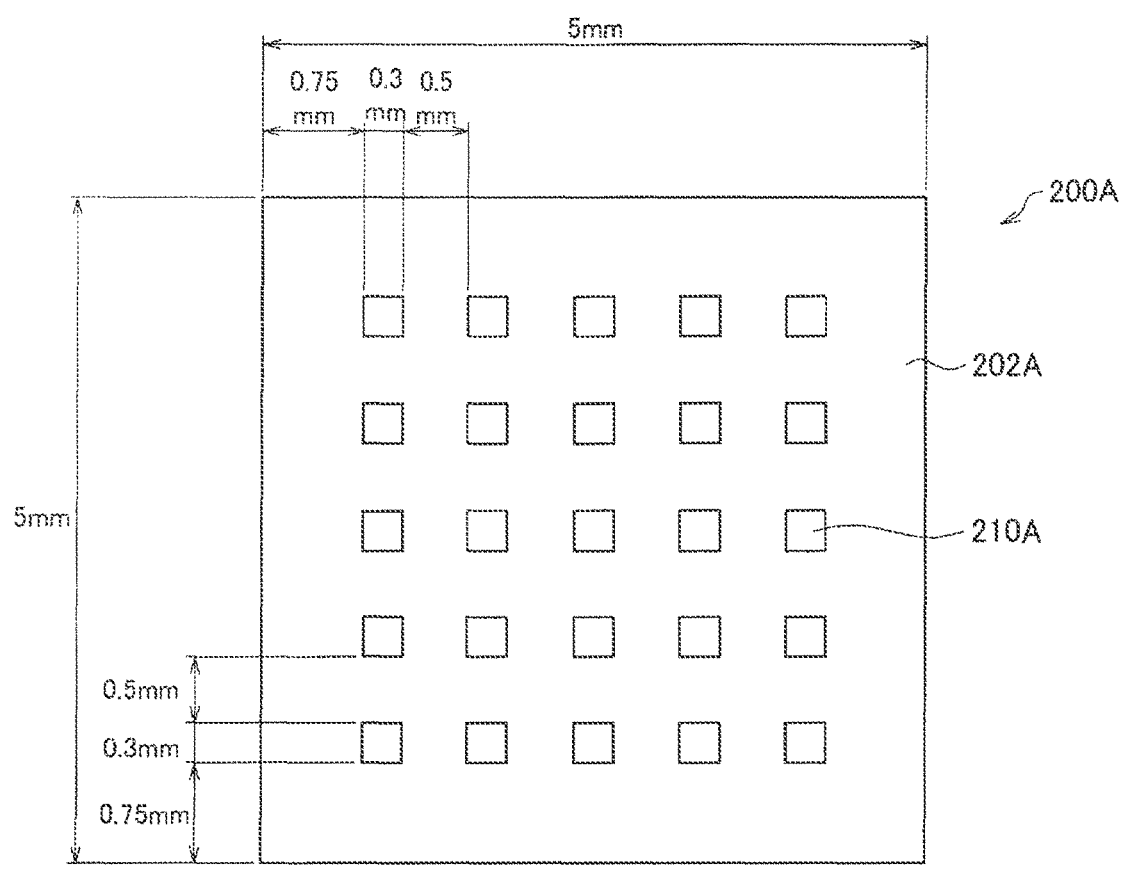
FIG. 22 is a front view of the fragrance cartridge according to the first modified example.

FIGS. 21 and 22 are illustrative diagrams showing a fragrance cartridge 200A according to a first modified example. FIG. 21 is a perspective view showing the fragrance cartridge 200A and an air flow channel 210A, and FIG. 22 is a front view of the fragrance cartridge 200A in which the number and size of the air flow channel 210A differ.

The fragrance cartridge 200A has a rectangular parallelepiped outer shape. The fragrance cartridge 200A has a plurality of air flow channels 210A formed in a longitudinal direction of a main body part 202A. The air flow channels 210A have a square-shaped cross-section and are arrayed vertically and horizontally at equal intervals. In the example illustrated in FIG. 21, the fragrance cartridge 200A has a cross-section with a size of 5 mm square and a length of 30 mm in the longitudinal direction. In addition, 10 air flow channels 210A each of which has a square-shaped cross-section with a side with a size of 200 μm (0.2 mm) are disposed both vertically and horizontally at equal intervals.

In addition, in the example illustrated in FIG. 22, the fragrance cartridge 200A has a cross-section with a size of 5 mm square, and 5 air flow channels 210A each of which has a square-shaped cross-section having a side with a size of 300 μm (0.3 mm) are disposed both vertically and horizontally at equal intervals with each interval being 0.5 mm. Note that it is possible to dispose 100 or more air flow channels 210A in the fragrance cartridge 200A having a cross-section with a size of 5 mm square if each of the air flow channels has a square-shaped cross-section with a size of 200 μm (0.2 mm) square.

The fragrance cartridge 200A also has the air flow channels 210A having a relatively small cross-sectional area and a liquid fragrance material is adhered to and held in inner surfaces of the air flow channels 210A. Thus, the fragrance cartridge 200A can stably hold a small amount of fragrance material. In addition, a fragrance material gasified at a high concentration can be emitted in a relatively small range by causing air to flow in the air flow channels 210A.

1-3-2. Second Modified Example

Figure 23:
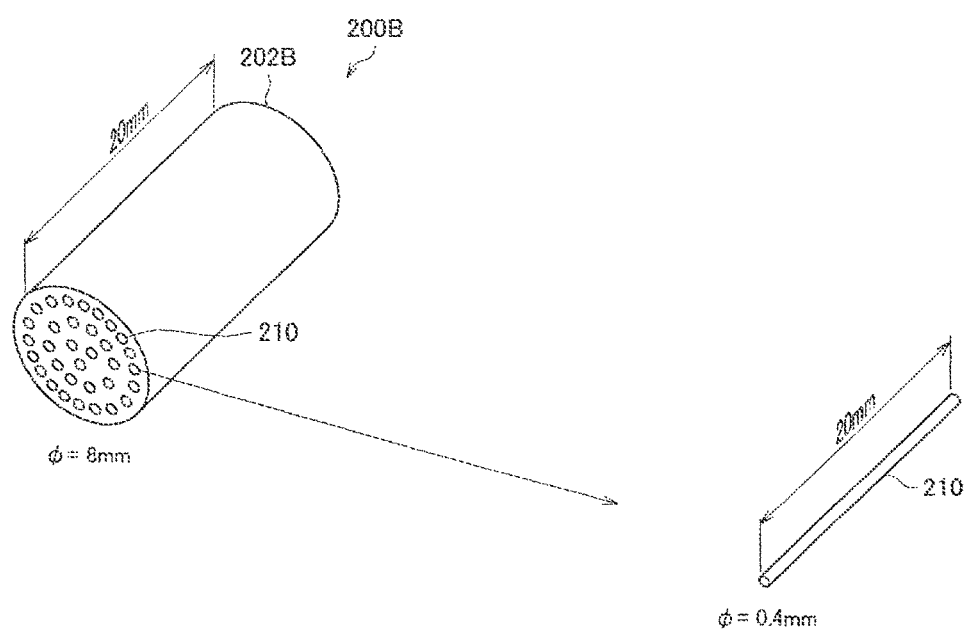
FIG. 23 is a perspective view showing a fragrance cartridge and air flow channels according to a second modified example of the embodiment.
Figure 24:
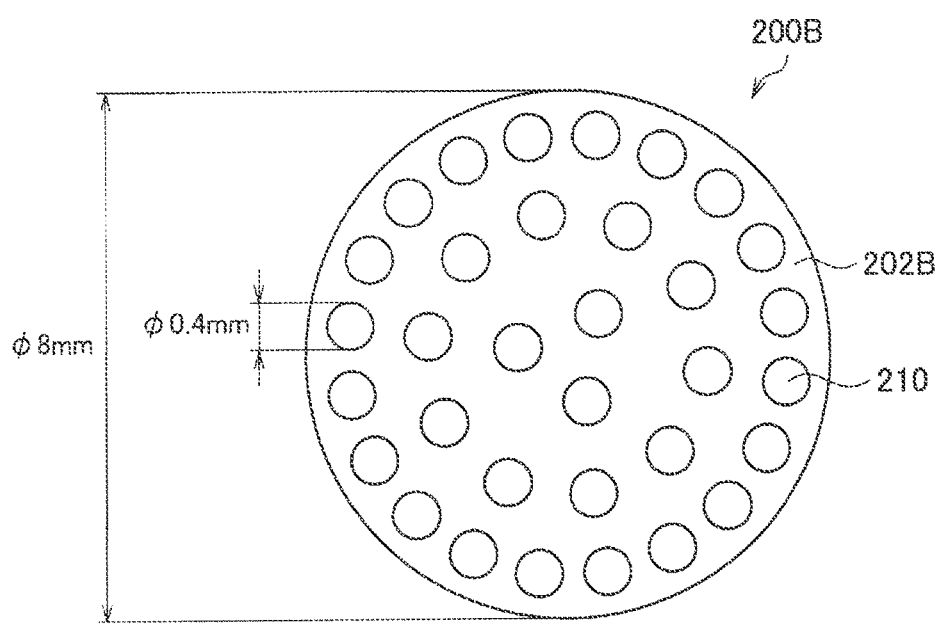
FIG. 24 is a front view of the fragrance cartridge according to the second modified example.

FIGS. 23 and 24 are illustrative diagrams showing a fragrance cartridge 200B according to a second modified example. FIG. 23 is a perspective view of the fragrance cartridge 200B and air flow channels 210B, and FIG. 24 is a front view of the fragrance cartridge 200B.

The fragrance cartridge 200B has a cylindrical outer shape. The fragrance cartridge 200B has a plurality of air flow channels 210B formed in a cylindrical outer shape in an axis line direction in a main body part 202B. While the fragrance cartridge 200 according to the above-described embodiment has a tubular shape having the axial hole 204, the fragrance cartridge 200B according to the second modified example does not have the axial hole 204 and the air flow channels 210B are disposed over an entire cross-section thereof.

In the example illustrated in FIGS. 23 and 24, the fragrance cartridge 200B has a circular cross-section with a diameter of 8 mm, and a length in the axial direction is 20 mm. In addition, the air flow channels 210B having a circular cross-section with a diameter of 400 μm (0.4 mm) are disposed on the circumferences of three concentric circles at equal intervals.

The fragrance cartridge 200B also has the air flow channels 210B having relatively small cross-sections and a liquid fragrance material is adhered to and held in inner surfaces of air flow channels 210B. Thus, the fragrance cartridge 200B can stably hold a small amount of fragrance material. In addition, a fragrance material gasified at a high concentration can be emitted in a relatively small range by causing air to flow in the air flow channels 210B.

Note that points other than those described above with respect to the fragrance cartridges 200A and 200B according to the first and second modified examples can be configured by appropriately combining with the configuration of the fragrance cartridge 200 according to the above-described embodiment.

1-4. Effects of First Embodiment

The perfuming device 1 according to the first embodiment of the present disclosure includes the fragrance cartridge 200 having the air flow channels 210 each of which has both ends open and of which at least a part of the inner surfaces thereof holds a fragrance material as described above. The fragrance cartridge 200 has the air flow channels 210 with a relatively small inner diameter, and thus a small amount of fragrance material can be stably held therein.

The fragrance cartridge 200 has the air flow channels 210 with a relatively small inner diameter and causes air to flow in the air flow channels 210 thereby gasifying and emitting a fragrance material along with the air. At this time, since the outlet opening from which the fragrance is emitted is relatively small, it is possible to narrow a diffusion flux of the emitted fragrance. In addition, the fragrance cartridge 200 has the air flow channels 210 having a high ratio of surface area with respect to volume and thus can gasify a small amount of fragrance material at a high concentration. Therefore, the perfuming device 1 according to the present embodiment can emit a highly concentrated fragrance over a narrow range when, for example, a person wants a fragrance for private use.

Furthermore, since the fragrance cartridge 200 has the air flow channels 210 with a relatively small inner diameter, the fragrance cartridge 200 can have a small outer shape, which enables the fragrance cartridge 200 or the perfuming device 1 to be carried with ease. In addition, since the fragrance cartridge 200 has the air flow channels 210 formed in the main body part 202 holding a fragrance material, it is not necessary to add the fragrance material dropwise each time of use.

In addition, when the air flow channels 210 of the fragrance cartridge 200 each have the branching section 216 or the merging section 218, it is possible to switch a fragrance emission channel or to mix a plurality of fragrances. Accordingly, an area necessary for emitting fragrances can be adjusted, amounts of fragrances can be adjusted, and thus the perfuming device 1 can be widely applied.

Furthermore, by providing the surface enlarging parts 260, 262, and 264 in the air flow channels 210 of the fragrance cartridge 200, an amount of fragrance materials held in the air flow channels 210 can be increased. Therefore, a life of the fragrance cartridge 200 can be lengthened.

Furthermore, the perfuming device 1 according to the present embodiment is used by mounting a replaceable fragrance cartridge 200, and an appropriate fragrance cartridge 200 can be selected in accordance with its application. Thus, the perfuming device 1 can be used in various applications such as enjoying different kinds of fragrance, varying a degree of fragrance diffusion, or the like.

2. Second Embodiment

Next, a fragrance cartridge according to a second embodiment of the present disclosure will be described. The fragrance cartridge according to the present embodiment is different from the fragrance cartridge according to the first embodiment in that a mask for switching an air flow channel in which air flows among a plurality of air flow channels is provided. The fragrance cartridge according to the present embodiment will be described below focusing on differences from the fragrance cartridge according to the first embodiment.

2-1. Basic Configuration

Figure 25:
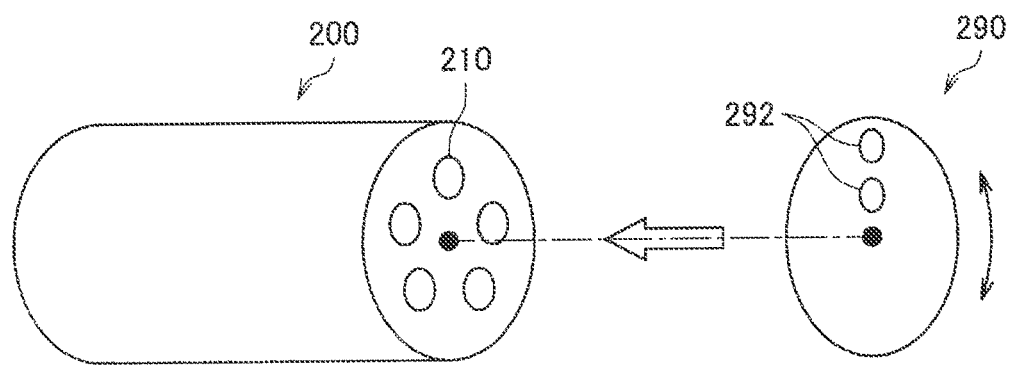
FIG. 25 is a perspective view showing a fragrance cartridge according to a second embodiment.

FIG. 25 is a schematic diagram showing a basic configuration of a fragrance cartridge 200 with a mask 290 according to a first example of the present embodiment. The fragrance cartridge 200 has a cylindrical outer shape and a plurality of air flow channels 210 are disposed on a circumference having an axis center as a center thereof. Although only 5 air flow channels 210 are illustrated in FIG. 25, the number of air flow channels 210 is not particularly limited. In addition, the fragrance cartridge 200 may have a plurality of air flow channels 210 disposed on each of a plurality of concentric circles having the axis center as a center thereof.

The mask 290 has at least one opening 292 and is rotatably attached to one end face of the fragrance cartridge 200. In the example of FIG. 25, the mask 290 is fixed to the axis center of the fragrance cartridge 200 and freely rotates around the axis center. The openings 292 provided on the mask 290 also rotate around the axis center in accordance with the rotation of the mask 290. Accordingly, it is possible to switch between opening and closing of the plurality of air flow channels 210 provided in the fragrance cartridge 200. Air supplied from an air pump or the like flows in the open air flow channels 210, and thereby a fragrance material held in the air flow channels 210 is gasified and emitted along with the air. In other words, an air flow channel 210 in which air flows or a fragrance to be emitted can be switched by rotating the mask 290.

In this case, the air supplied by the air pump or the like may be supplied to the entire one end face of the fragrance cartridge 200, rather than being supplied to only one air flow channel 210 as illustrated in FIG. 2 or the like. Air does not pass through an air flow channel 210 closed by the mask 290 in the state in which the air is supplied to an entire one end face of the fragrance cartridge 200. The mask 290 may be disposed on an end face of the fragrance cartridge 200 at a side in which air is introduced (an inlet side) or an end face thereof at a side in which air is emitted (an outlet side). However, if the mask 290 is disposed at the inlet side of the fragrance cartridge 200, the mask 290 is depressed toward the fragrance cartridge 200 by air supplied to the end face of the inlet side, and accordingly a closed air flow channel 210 can be tightly shielded.

Rotation of the mask 290 may be manually performed, or may be performed by a driving device using power, for example, from an electro-magnetic motor, a piezo-electric element, a magnet, an aerodynamic actuator, an electoactive polymer (EAP), or the like. In addition, in the present embodiment, although an example in which the circulardisk-like mask 290 is provided in the cylindrical fragrance cartridge 200 has been described, a shape of the mask is not limited to a circular disk and may be appropriately selected in accordance with a shape of the end face of the fragrance cartridge.

As a constituent material of the mask 290, for example, one kind or a plurality of kinds of material among a polymeric resin such as an acrylic resin, a urethane resin, an ABS resin, a polyetheretherketone (PEEK) resin, a polyacetal (POM) resin, a silicone resin, a fluorine resin, a cycloolefin polymer resin, or a polyimide resin, a metal such as stainless steel or aluminum, an inorganic crystalline material such as quartz, and glass can be used, like a constituent material of the fragrance cartridge 200. A constituent material of the mask 290, however, is not limited to the above-described examples.

2-2. First Example

Figure 26:
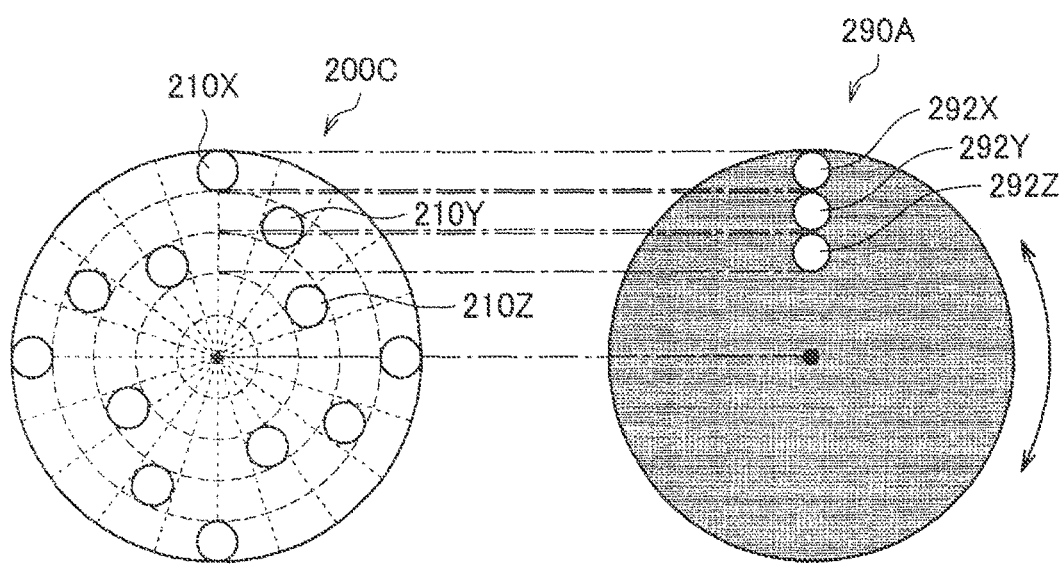
FIG. 26 is an illustrative diagram showing air flow channels of the fragrance cartridge and openings of a mask according to the embodiment.

FIG. 26 is a schematic diagram showing a fragrance cartridge 200C having a mask 290A as a first example of the fragrance cartridge according to the present embodiment. FIG. 26 is an illustrative diagram showing a relationship between openings of air flow channels 210X, 210Y, and 210Z provided in the fragrance cartridge 200C and openings 292X, 292Y, and 292Z of the mask 290A.

The fragrance cartridge 200C has the plurality of air flow channels 210X, 210Y, and 210Z that are open in three concentric circles having an axis center as a center. Four of each of the air flow channels 210X, 210Y, and 210Z open in the circumferences of the circles at equal intervals. In other words, the respective air flow channels 210X, 210Y, and 210Z are open at intervals having an angle of 90° C. therebetween. In addition, the openings of the plurality of air flow channels 210X, 210Y, and 210Z are disposed on the same lines extending from the axis center in radial directions such that the plurality of openings do not overlap.

The mask 290A has three openings 292X, 292Y, and 292Z. The three openings 292X, 292Y, and 292Z are disposed on the same line extending from a center point in a radial direction. A distance from the center point of the mask 290A to each of the openings 292X, 292Y, and 292Z is substantially identical to a distance from the axis center of the fragrance cartridge 200C to each of the air flow channels 210X, 210Y, and 210Z. In other words, the opening 292X opens or closes the air flow channels 210X, the opening 292Y opens or closes the air flow channels 210Y, and the opening 292Z opens or closes the air flow channels 210Z.

In the fragrance cartridge 200C of the first example, any one of the plurality of air flow channels 210X, 210Y, and 210Z can overlap any one of the three openings 292X, 292Y, and 292Z of the mask 290A by rotating the mask 290A. Thus, an air flow channel in which air flows can be switched among the 12 air flow channels 210X, 210Y, and 210Z provided in the fragrance cartridge 200C.

Figure 27:
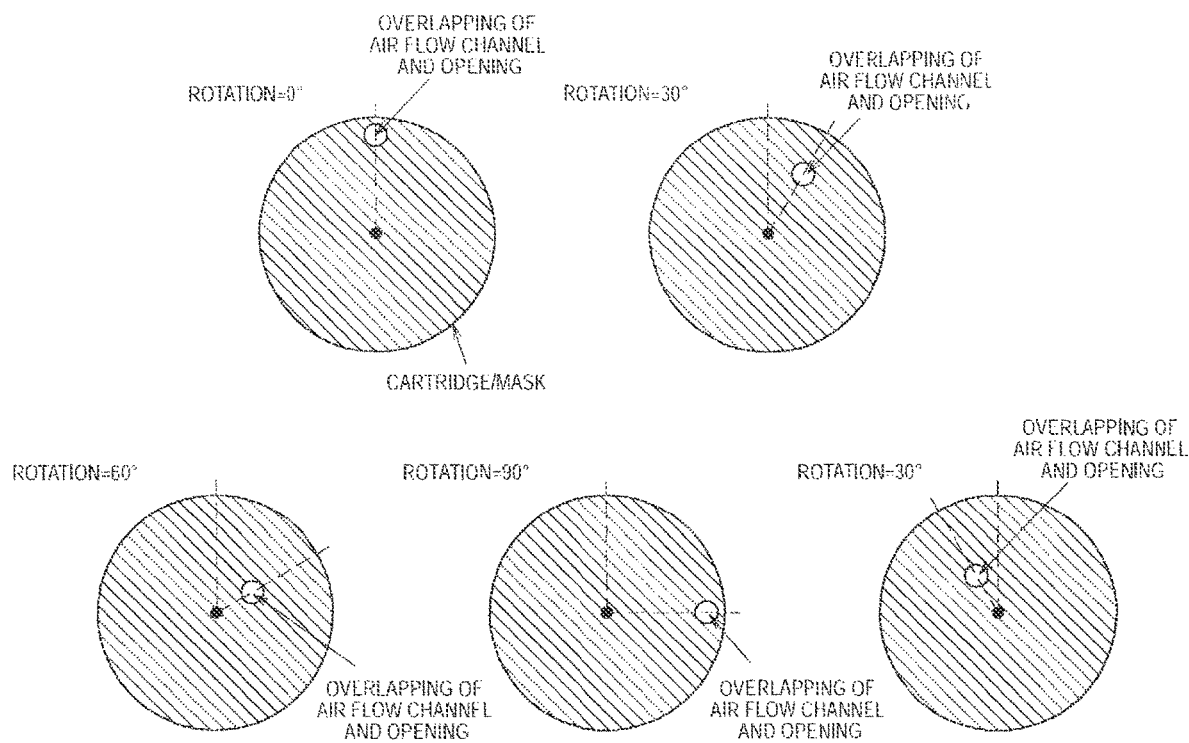
FIG. 27 is an illustrative diagram showing rotation angles of the mask and open positions of the air flow channels.

FIG. 27 is an illustrative diagram showing open air flow channels differing in accordance with rotation angles of the mask 290A in the fragrance cartridge 200C according to the first example. FIG. 27 shows the air flow channels 210X, 210Y, and 210Z of the fragrance cartridge 200C disposed as illustrated in FIG. 26 and a state of the mask 290A shown in FIG. 26 at a rotation angle of 0°. As illustrated in FIG. 27, in the fragrance cartridge 200C according to the first example, the air flow channels 210X, 210Y, and 210Z to be open can be made to differ by shifting the rotation angle of the mask 290A by 30°.

In this case, for example, a driving device may be set to rotate the mask 290A by 30°, and the mask 290A may be rotated a predetermined angle in accordance with the number of operations of pressing a switch of the driving device.

In the fragrance cartridge 200C according to the first example of the first embodiment, the air flow channels 210X, 210Y, and 210Z in which air flows can be switched between by rotating the mask 290A as described above, and a fragrance to be emitted can be selected in accordance with a mood of a user at the time of use.

2-3. Second Example

Figure 28:
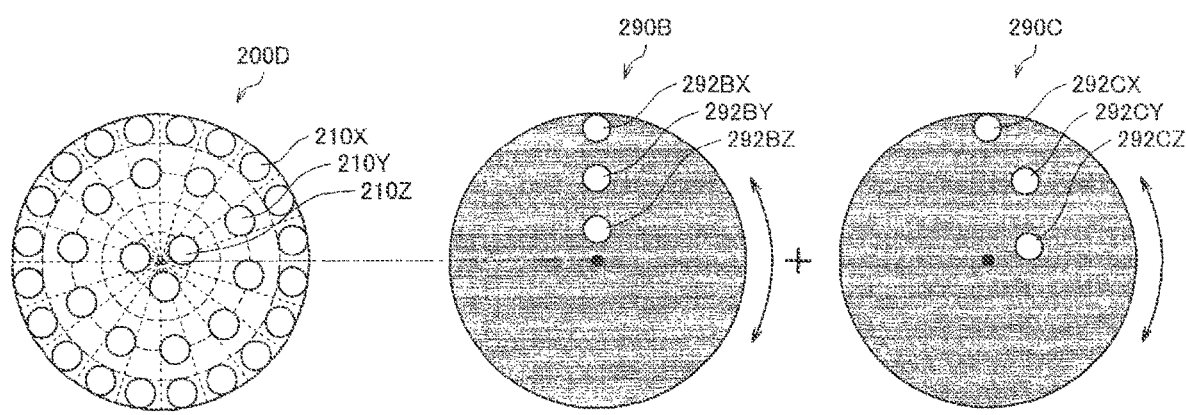
FIG. 28 is an illustrative diagram showing air flow channels of a fragrance cartridge and openings of a mask according to a first modified example of the embodiment.

FIG. 28 is a schematic diagram showing a fragrance cartridge 200D with two masks 290B and 290C as a second example of the fragrance cartridge according to the present embodiment. FIG. 28 is an illustrative diagram showing a positional relationship between openings of air flow channels 210X, 210Y, and 210Z provided in the fragrance cartridge 200D, openings 292BX, 292BY, and 292BZ of the first mask 290B, and openings 292CX, 292CY, and 292CZ of the second mask 290C.

The fragrance cartridge 200D has a plurality of air flow channels 210X, 210Y, and 210Z that are open in three concentric circles having an axis center as a center. 20 openings of the air flow channel 210X are disposed on a circumference at equal intervals (having an angle of 18° therebetween). 10 openings of the air flow channels 210Y are disposed on a circumference at equal intervals (having an angle of 36° therebetween). 3 openings of the air flow channels 210Y are disposed on a circumference at equal intervals (having an angle of 120° therebetween). Some of the air flow channels 210X, 210Y, and 210Z are disposed on the same lines extending from the axis center in radial directions.

The first mask 290B has the three openings 292BX, 292BY, and 292BZ. The three openings 292BX, 292BY, and 292BZ are disposed on the same line extending from the center point in a radial direction. A distance from the center point of the first mask 290B to each of the openings 292BX, 292BY, and 292BZ is substantially identical to a distance from the axis center of the fragrance cartridge 200D to each of the air flow channels 210X, 210Y, and 210Z.

The second mask 290C has the three openings 292CX, 292CY, and 292CZ. In the second mask 290C, the different openings 292CX, 292CY, and 292CZ are disposed such that the openings do not overlap the same lines extending from the center point in radial directions. In other words, the plurality of openings 292CX, 292CY, and 292CZ each of which is disposed on a circumference of the corresponding concentric circle are disposed such that one of the openings 292CX, 292CY, and 292CZ does not overlap an area surrounded by two lines that are parallel to a line connecting the center point of the second mask 290C and a center point of another of the openings 292CX, 292CY, and 292CZ and that adjoin the other of the openings 292CX, 292CY, and 292CZ.

In the fragrance cartridge 200D according to a second modified example, only one air flow channel among the 33 air flow channels 210X, 210Y, and 210Z provided in the fragrance cartridge 200D is opened by changing a rotation angle of each of the first mask 290B and the second mask 290C.

Figure 29:
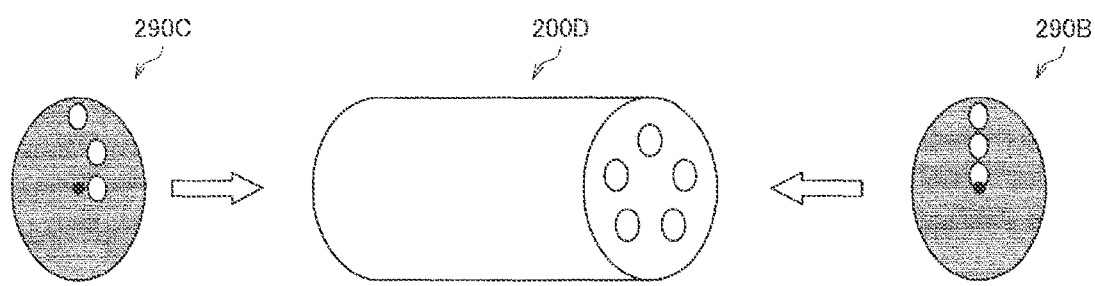
FIG. 29 is a perspective view showing the fragrance cartridge according to the first modified example of the embodiment.
Figure 30:
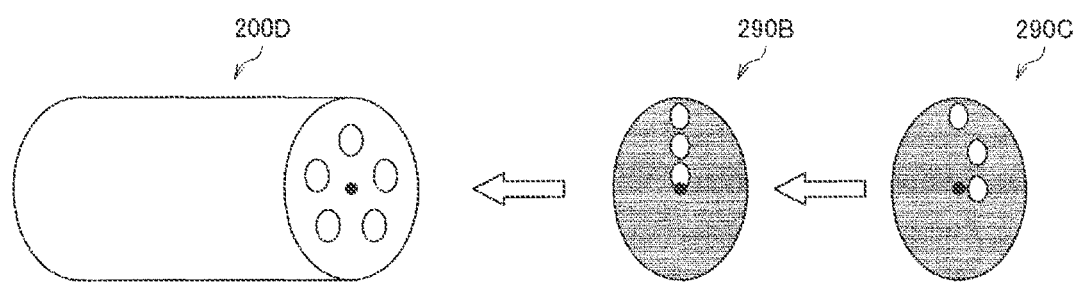
FIG. 30 is a perspective view showing the fragrance cartridge according to the first modified example of the embodiment.

As illustrated in FIG. 29, the first mask 290B and the second mask 290C may both be disposed on one end face among two end faces of the fragrance cartridge 200D. Alternatively, the first mask 290B or the second mask 290C may be disposed on both end faces of the fragrance cartridge 200D as illustrated in FIG. 30.

FIG. 31 is an illustrative diagram showing that open air flow channels differ in accordance with rotation angles of the first mask 290B and the second mask 290C in the fragrance cartridge 200D according to the second example. FIG. 31 shows the air flow channels 210X, 210Y, and 210Z of the fragrance cartridge 200D disposed as illustrated in FIG. 28 and a state of the first mask 290B and the second mask 290C shown in FIG. 28 at a rotation angle of 0°. As illustrated in FIG. 31, in the fragrance cartridge 200D according to the second example, the air flow channels 210X, 210Y, and 210Z to be open can be made to differ by shifting rotation angles of the first mask 290B and the second mask 290C by 18°.

In this case, for example, the driving device may be set to rotate the first mask 290B and the second mask 290C by 18° and thus the first mask 290B and the second mask 290C may each be rotated a predetermined angle in accordance with the number of operations of pressing a switch of the driving device. By rotating the first mask 290B and the second mask 290C in this manner in the fragrance cartridge 200D according to the second example of the present embodiment, the air flow channels 210X, 210Y, and 210Z in which air flows can be switched between and a fragrance to be emitted can be selected in accordance with a mood of a user at the time of use.

Note that, when air flow channels 210X, 210Y, and 210Z are disposed in a fragrance cartridge 200E as exemplified in FIG. 32, the air flow channels 210X, 210Y, and 210Z may all be closed in a state in which a mask 290D is placed at a certain rotation angle. In the example of FIG. 32, when the illustrated fragrance cartridge 200E is set to overlap the mask 290D, all of the air flow channels 210X, 210Y, and 210Z are closed and thus none of the air flow channels allows air to pass therethrough. Accordingly, when the perfuming device is not used, hardly any of a fragrance material held in the air flow channels 210X, 210Y, and 210Z is able to leak out.

2-4. Modified Example

Figure 33:
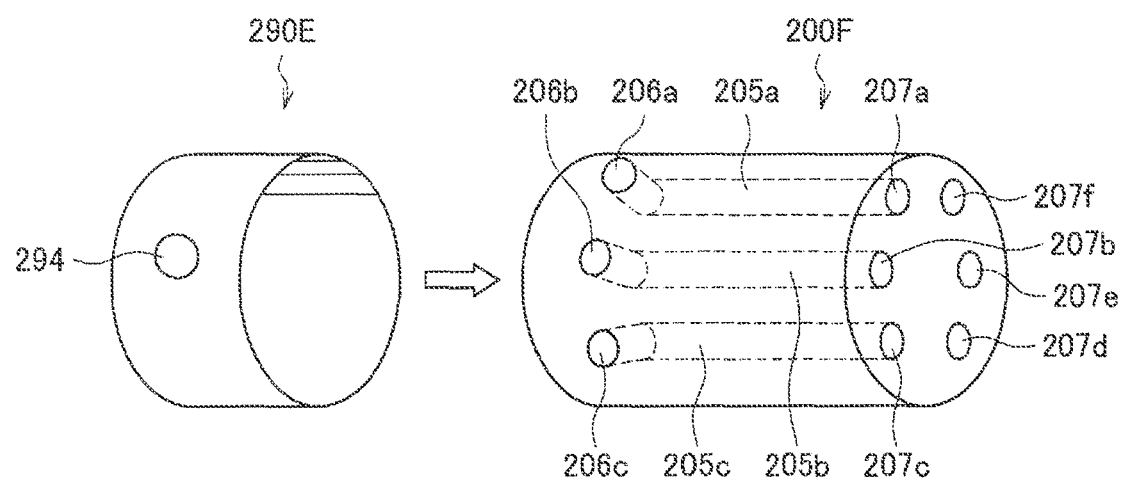
FIG. 33 is a perspective diagram showing a fragrance cartridge according to a second modified example of the embodiment.

FIG. 33 is an illustrative diagram showing a fragrance cartridge 200F according to a modified example of the present embodiment. The fragrance cartridge 200F according to the modified example has a plurality of air flow channels 205a to 205c of which openings 207a to 207f at one end side are formed in an end part of the fragrance cartridge 200F in an axial direction and openings 206a to 206c at the other end side are formed on an outer circumferential surface of the fragrance cartridge 200F. In FIG. 33, only three air flow channels 205a to 205c among six air flow channels are illustrated.

In addition, a mask 290E that opens or closes the air flow channels 205a to 205c has a cap shape and is mounted on the fragrance cartridge 200F from the end side among both ends of the fragrance cartridge 200F on which the openings 206a to 206c of the air flow channels 205a to 205c are formed on the outer circumferential surface. The cap-shaped mask 290E is designed to be axially rotatable using an axis center of the fragrance cartridge 200F as a center.

The cap-shaped mask 290E has an opening 294 on its circumferential surface. The opening 294 can overlap any one of the openings 206a to 206c of the air flow channels 205a to 205c among the plurality of air flow channels 205a to 205c by axially rotating the mask 290E. Thus, by changing a rotation angle of the cap-shaped mask 290E, the air flow channels 205a to 205c through which air passes can be switched between.

Figure 34:
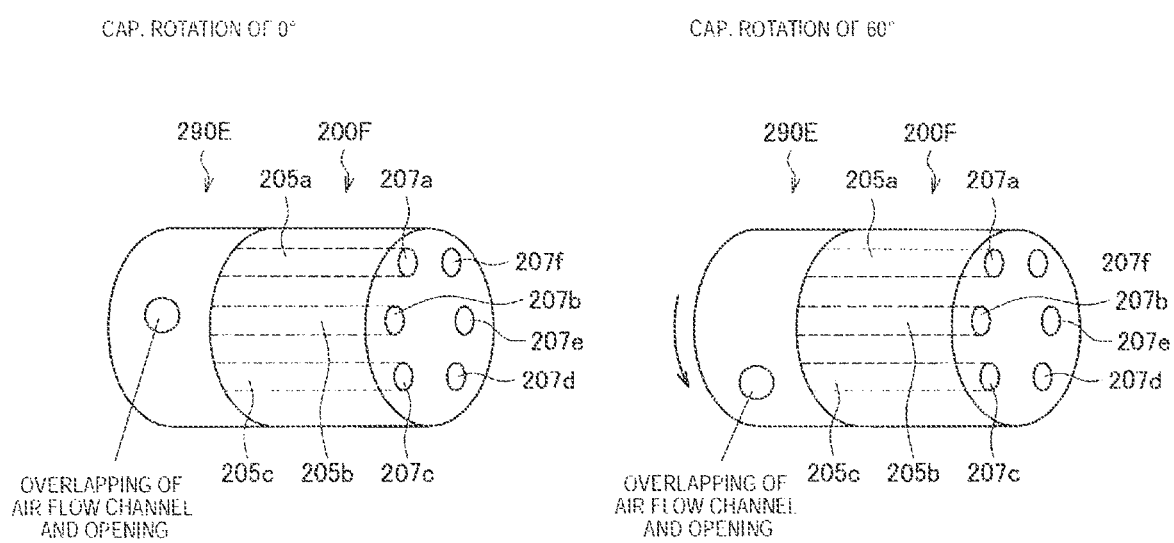
FIG. 34 is an illustrative diagram showing rotation angles of a cap-shaped mask and open positions of air flow channels.

FIG. 34 is an illustrative diagram showing switching of an air flow channel to be opened in accordance with a rotation angle of the cap-shaped mask 290E in the fragrance cartridge 200F according to the modified example. FIG. 34 shows the air flow channels 205a to 205c of the fragrance cartridge 200F disposed as illustrated in FIG. 33 and a state of the cap-shaped mask 290E shown in FIG. 33 at a rotation angle of 0°. As shown in FIG. 33, the air flow channels 205a to 205c to be opened can be switched between by shifting the rotation angle of the cap-shaped mask 290E by 60° in the fragrance cartridge 200F according to the modified example.

Also in this case, for example, a driving device may be set to rotate the cap-shaped mask 290E by 60° and thus the mask 290E may be rotated a predetermined angle in accordance with the number of operations of pressing a switch of the driving device. In addition, all of the air flow channels 205a to 205c can be closed when the mask 290E is held in a position in which the opening 294 of the mask 290E does not overlap the openings 206a to 206c of the air flow channels 205a to 205c. By rotating the cap-shaped mask 290E in the fragrance cartridge 200F according to the modified example of the present embodiment, the air flow channels 205a to 205c in which air flows can be switched between and thus a fragrance to be emitted can be selected in accordance with a mood of a user at the time of use.

2-5. Effects of Second Embodiment

As described above, the fragrance cartridge according to the second embodiment of the present disclosure can switch an air flow channel in which air flows among the plurality of air flow channels by rotating the mask. Thus, it is possible to switch an air flow channel through which air passes while supplying air to an entire face at one end side of the fragrance cartridge. Accordingly, the air flow channel through which air passes can be easily switched by rotating the mask and thus a fragrance to be emitted can be easily selected.

Note that the basic configuration of the fragrance cartridge according to the present embodiment can be the same as that of the fragrance cartridge according to the first embodiment. Thus, the fragrance cartridge according to the present embodiment can obtain the same effects as those obtained from the fragrance cartridge according to the first embodiment.

3. Third Embodiment

Next, an example of a sales system for the fragrance cartridge described in the first and second embodiments will be described.

Figure 35:
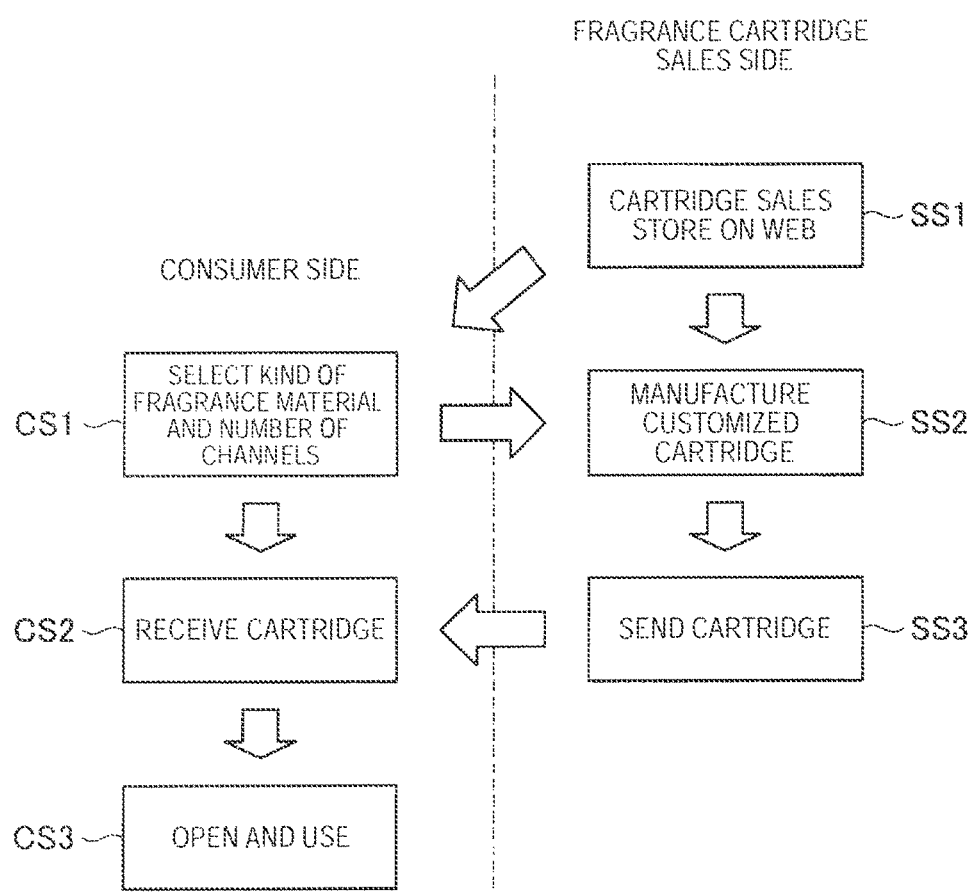
FIG. 35 is an explanatory diagram showing an example of a sales system for fragrance cartridges.

FIG. 35 shows an example of a case of fragrance cartridges sold on the Internet and a sales procedure performed by a seller and a consumer of the fragrance cartridges. The seller of the fragrance cartridges establishes a website of an on-line store that consumers can access via the Internet (Step SS1). A consumer accesses the website and selects, for example, kinds of fragrance materials or the number of air flow channels of a fragrance cartridge. Specifically, the consumer selects the total number of air flow channels provided in the fragrance cartridge from a prepared product line-up and freely selects air flow channels that will hold the fragrance materials in accordance with his or her preference.

After deciding the specification of the fragrance cartridge, the consumer confirms an on-line order process (Step CS1).

The seller who has received the order manufactures a customized fragrance cartridge on the basis of the details of the order (Step SS2). The seller, for example, causes the designated liquid fragrance materials to be held on an inner surface of the air flow channels by injecting the fragrance materials into the predetermined air flow channels of the fragrance cartridge selected by the consumer, blowing air into the air flow channels, and causing a surplus of the fragrance materials to be discharged. The injection of the fragrance materials may be automatically performed by a dedicated injection device after the on-line order process is received. The manufactured customized fragrance cartridge is delivered to the consumer (Step SS3). At this time, the fragrance cartridge may be enclosed in a tightly closed container or packaged and delivered. In addition, a packaging container or a package of the fragrance cartridge may have a light-shielding property or the fragrance cartridge may be enclosed and dehumidified. The consumer receives the fragrance cartridge (Step CS2), installs the fragrance cartridge in a perfuming device and uses it (Step CS3).

Figure 36:
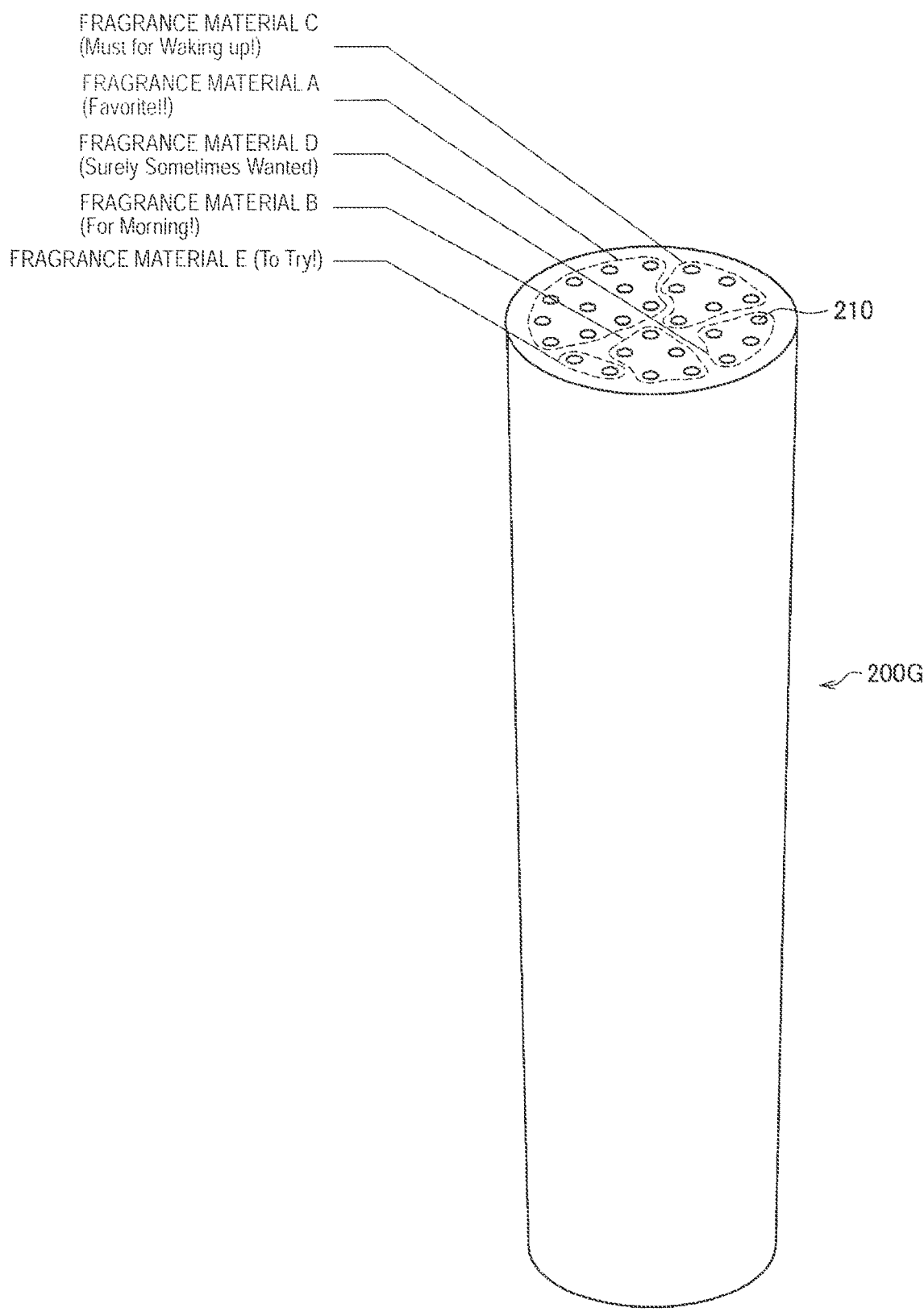
FIG. 36 is an illustrative diagram showing an example of disposition of fragrance materials in a fragrance cartridge.
Figure 37:
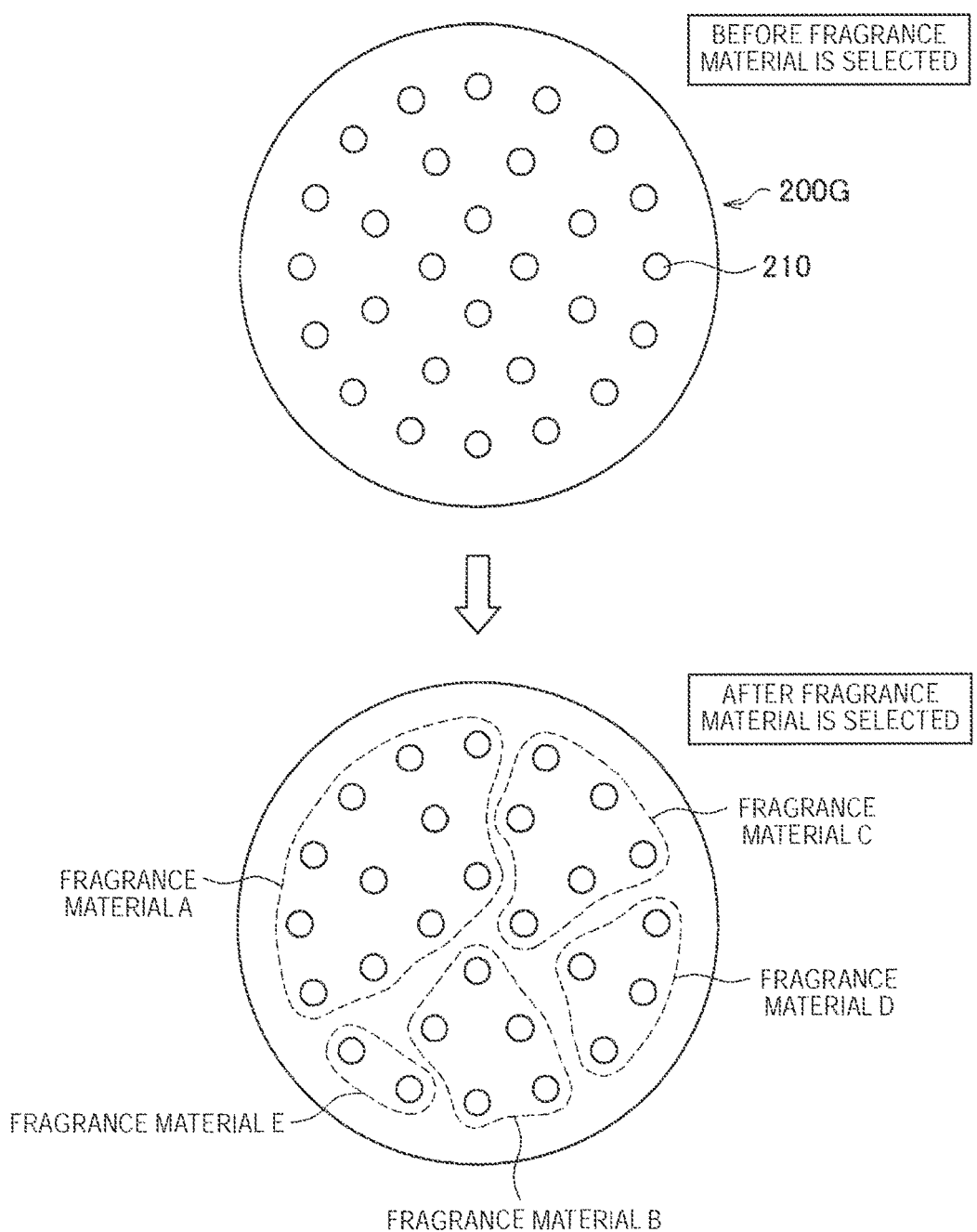
FIG. 37 is an illustrative diagram showing an example of disposition of fragrance materials in a fragrance cartridge.

FIGS. 36 and 37 show an example of a customized fragrance cartridge 200G. The fragrance cartridge 200G has 28 air flow channels 210. A plurality of kinds of fragrance material such as fragrance material A named "Favorite," a fragrance material B named "For Morning," a fragrance material C named "Must for Waking up," a fragrance material D named "Surely Sometimes Wanted," and a fragrance material E named "To Try" can be selected on a website.

A consumer selects an appropriate fragrance material for his or her preference from the types of fragrance material and designates an air flow channel that will hold each of the fragrance materials. Accordingly, an original fragrance cartridge suitable for the preference of the consumer is manufactured.

The purchase price of the fragrance cartridge may be paid online for a series of transactions. In addition, when the prepared product lineup does not include a preferred fragrance material, a self-blended fragrance material or any of various brands of fragrance material can be designated. In addition, a fragrance cartridge holding a plurality of pre-selected fragrance materials can be selected, in addition to allowing consumers to select the number of air flow channels or fragrance materials. Furthermore, used fragrance cartridges may be returned to the seller, washed, and reused.

According to the sales system for fragrance cartridges exemplified above, consumers can freely select fragrance materials for their preference and receive original fragrance cartridges. In addition, consumers can easily customize fragrances online and order their original fragrance cartridges. Further, consumers can order fragrance cartridges online and take delivery thereof, and thus it is not necessary to visit shops and the like in person.

In addition, the seller side can accumulate and analyze detailed data of fragrance materials preferred by purchasers. Furthermore, by systemizing a process of receiving orders and manufacturing fragrance cartridges, the seller can manufacture and sell the fragrance cartridges without accumulating a large amount of inventory.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Additionally, the present technology may also be configured as below.

(1)

A cartridge for a perfuming device, including:
a main body part;
an air flow channel that is provided in the main body part and has both ends that are open; and
a fragrance material held in at least a part of an inner surface of the air flow channel.

(2)

The cartridge for a perfuming device according to (1), in which an inner diameter of the air flow channel has a value in the range of 10 to 1,000 μm.

(3)

The cartridge for a perfuming device according to (1) or (2), including
a plurality of air flow channels.

(4)

The cartridge for a perfuming device according to any one of (1) to (3), in which an outlet opening of the air flow channel has a tapered shape in which a diameter increases toward an opening end.

(5)

The cartridge for a perfuming device according to any one of (1) to (4), in which an inlet opening of the air flow channel has a tapered shape in which a diameter increases toward an opening end.

(6)

The cartridge for a perfuming device according to any one of (1) to (5), in which the air flow channel branches at least at one branching section and has a plurality of outlet openings.

(7)

The cartridge for a perfuming device according to any one of (1) to (6), in which the air flow channel has a plurality of inlet openings which merge at least at one merging section.

(8)

The cartridge for a perfuming device according to any one of (1) to (7), including:
a plurality of air flow channels; and
a mask having at least one opening for opening some air flow channels of the plurality of air flow channels.

(9)

The cartridge for a perfuming device according to (8), in which the mask is rotatably supported.

(10)

The cartridge for a perfuming device according to (8) or (9), in which a plurality of masks are provided on one or both of a surface on which an inlet opening of the air flow channel is provided and a surface on which an outlet opening of the air flow channel is provided.

(11)

The cartridge for a perfuming device according to any one of (8) to (10), in which, when a plurality of masks are provided, only one opening is opened by switching positions of the plurality of masks.

(12)

The cartridge for a perfuming device according to any one of (8) to (11), in which inlet openings or outlet openings of the plurality of air flow channels are disposed on circumferences of a plurality of concentric circles having different diameters, and openings of the mask are provided on circumferences of the plurality of concentric circles.

(13)

The cartridge for a perfuming device according to (12), in which the mask has a plurality of openings each of which is disposed on the circumference of the corresponding concentric circle.

(14)

The cartridge for a perfuming device according to (13), in which the plurality of openings each of which is disposed on the circumference of the corresponding concentric circle are disposed on a line extending from a center point of the mask in a predetermined radial direction.

(15)

The cartridge for a perfuming device according to (13), in which the plurality of openings each of which is disposed on the circumference of the corresponding concentric circle are disposed such that one of the openings does not overlap an area surrounded by two lines that are parallel to a line connecting a center point of the mask and a center point of another of the openings and that adjoin the other of the openings.

(16)

The cartridge for a perfuming device according to any one of (1) to (15), in which the air flow channel has surface enlarging parts that enlarge a surface inside the channel.

(17)

The cartridge for a perfuming device according to (16), in which the surface enlarging parts have a rotation-symmetric structure with respect to an axial center of the air flow channel, a translation-symmetric structure in an axial direction of the air flow channel, and a reflection-symmetric structure in the axial direction of the air flow channel.

(18)

The cartridge for a perfuming device according to (16) or (17), in which, when the air flow channel is viewed in an axial direction, the surface enlarging parts have a grid shape in which the surface enlarging parts intersect on a predetermined axis.

(19)

A perfuming device including:
  a cartridge including a main body part, an air flow channel that is provided in the main body part and has both ends that are open, and a fragrance material held in at least a part of an inner surface of the air flow channel; and
  an air blowing part that supplies air to the air flow channel of the cartridge.

(20)

The perfuming device according to (19),
  in which the cartridge includes a plurality of air flow channels, and
  the perfuming device includes an actuator for rotating a mask having at least one opening for opening some air flow channels of the plurality of air flow channels.

The invention claimed is:

1. A cartridge for a perfuming device, comprising:
  a main body part;
  a plurality of air flow channels provided in the main body part and each having both ends that are open, each air flow channel having a tapered shape outlet opening in which a diameter increases toward an opening end; and
  a fragrance material held in at least a part of an inner surface of the air flow channel,
  wherein the outlet openings of the plurality of air flow channels are disposed on circumferences of a plurality of concentric circles having different diameters.

2. The cartridge for a perfuming device according to claim 1, wherein an inner diameter of the air flow channel has a value in the range of 10 to 1,000 µm.

3. The cartridge for a perfuming device according to claim 1, wherein an inlet opening of the air flow channel has a tapered shape in which a diameter increases toward an opening end.

4. The cartridge for a perfuming device according to claim 1, wherein the air flow channel branches at least at one branching section and has a plurality of outlet openings.

5. The cartridge for a perfuming device according to claim 1, wherein the air flow channel has a plurality of inlet openings which merge at least at one merging section.

6. The cartridge for a perfuming device according to claim 1, wherein the air flow channel has surface enlarging parts that enlarge a surface inside the channel.

7. The cartridge for a perfuming device according to claim 6, wherein the surface enlarging parts have a rotation-symmetric structure with respect to an axial center of the air flow channel, a translation-symmetric structure in an axial direction of the air flow channel, and a reflection-symmetric structure in the axial direction of the air flow channel.

8. The cartridge for a perfuming device according to claim 6, wherein, when the air flow channel is viewed in an axial direction, the surface enlarging parts have a grid shape in which the surface enlarging parts intersect on a predetermined axis.

9. A perfuming device comprising:
  a cartridge including a main body part, a plurality of air flow channels provided in the main body part and each having both ends that are open, each air flow channel having a tapered shape outlet opening in which a diameter increases toward an opening end, and a fragrance material held in at least a part of an inner surface of the air flow channel; and
  an air blowing part that supplies air to the air flow channel of the cartridge,
  wherein the outlet openings of the plurality of air flow channels are disposed on circumferences of a plurality of concentric circles having different diameters.

* * * * *